(12) United States Patent
Al Soud

(10) Patent No.: US 10,842,829 B2
(45) Date of Patent: Nov. 24, 2020

(54) NATURAL PRODUCT TO IMPROVE IMMUNITY AND COMBAT VIRAL DISEASES, BACTERIAL DISEASES, FUNGAL DISEASES, AND CANCER DISEASES

(71) Applicant: Malek Al Soud, Izraa (SY)

(72) Inventor: Malek Al Soud, Izraa (SY)

( * ) Notice: Subject to any disclaimer, the term of this patent is extended or adjusted under 35 U.S.C. 154(b) by 0 days.

(21) Appl. No.: 16/686,989

(22) Filed: Nov. 18, 2019

(65) Prior Publication Data

US 2020/0078416 A1   Mar. 12, 2020

Related U.S. Application Data

(63) Continuation-in-part of application No. PCT/IB2017/055445, filed on Sep. 9, 2017.

(51) Int. Cl.
*A61K 35/74*   (2015.01)
*A61K 36/60*   (2006.01)

(52) U.S. Cl.
CPC .............. *A61K 35/74* (2013.01); *A61K 36/60* (2013.01)

(58) Field of Classification Search
None
See application file for complete search history.

(56) References Cited

U.S. PATENT DOCUMENTS

2016/0051596 A1 *   2/2016   Chen ...................... A61K 35/74
                                                                424/93.4

OTHER PUBLICATIONS

Afr. J. Microbiol, Res., 2013(7), pp. 2332-2338.
J. Mater, Environ, Sci., 2013(4), pp. 33-38.
eCAM, 2013, pp. 1-8.
IRJP 2011(2), pp. 124-127.

* cited by examiner

*Primary Examiner* — Blaine Lankford
(74) *Attorney, Agent, or Firm* — Miller Law Group, PLLC

(57) ABSTRACT

A natural product for improving health and reducing the risk of death due to dangerous diseases comprises a presence of figs and *Acetobacter pasteurianus*.

7 Claims, 14 Drawing Sheets

NATURAL PRODUCT TO IMPROVE IMMUNITY AND COMBAT VIRAL DISEASES, BACTERIAL DISEASES, FUNGAL DISEASES, AND CANCER DISEASES

This is a continuation-in-part application which claims the benefit under 35 U.S.C. 365(c) of international application serial no. PCT/IB2017/055445 filed Sep. 9, 2017, which is incorporated by reference herein.

FIELD OF INVENTION

The present invention relates to composition for health improvement from natural resources.

BACKGROUND ART

Early this century, the number of cancer patients were increased. There are several types such as brain cancer, kidney cancer, and lung cancer. The patients suffered badly throughout their disease. where the tumor was first removed, then—radiotherapy, followed by chemotherapy. Cancer patient was losing the life slowly. Thus, the Microbiology creatures that feed on these plants obtain the plants' medical benefits.

The viral diseases have no known cure. The scientists and researchers must to invent an effective medicine against all serious diseases. Most importantly, the product presented treatment for cancer. Currently, cancer patient undergoing modern treatment using radiotherapy, chemotherapy etc suffers from the side effect and also the treatment affect healthy tissues.

Patient suffers from the side effect and also the treatment affect healthy tissues by radiotherapy, chemotherapy.

This invention is about making a new drug for humans, they are in a dire need for it. Countries have spent billions of dollars to make drugs to treat cancer or kill viruses or bacteria that resist medicines or cause dangerous diseases.

SUMMARY OF THE INVENTION

An aspect of the invention to is to provide a pharmaceutical composition for health improvement comprising of extract of fermented figs with microorganism (when grows on the figs or solid medium which contains at liquid of fig).

Preferably, the microorganism is *Acetobacter pasteurianus*.

Advantageously, the pharmaceutical composition is made from natural resources.

Advantageously, the pharmaceutical composition have no side effect.

Advantageously, the extract fermented figs by *Acetobacter pasteurianus* (when grows on the figs or solid medium which contains at liquid of fig) having active ingredient exhibits anti-cancer, anti-inflammatory, anti-viral, anti-fungal, anti-bacteria, and strengthen immune system property.

The extracts of *Acetobacter pasteurianus* (such as enzymes and secretions) inside the product, in addition to some of the resulting substances after the growth of *Acetobacter pasteurianus* on the figs.

The extracts of figs fermented by *Acetobacter pasteurianus*, addition to extract of *Acetobacter pasteurianus*.

According to another aspect of the present invention there is provided a pharmaceutical compound comprising a presence of figs and *Acetobacter pasteurianus*.

Preferably the pharmaceutical compound is produced from the extracts of the *Acetobacter pasteurianus* when it grows on a solid medium made of Nitrate Agar with fig liquid.

Preferably the *Acetobacter pasteurianus* grows on the figs and the *Acetobacter pasteurianus* feeds on substances in the figs.

Preferably the composition is produced by fermentation of the figs by microorganisms (the *Acetobacter pasteurianus*).

Preferably the composition is for use to improve immune response.

Preferably the composition is for use in inflammatory treatment.

Preferably, *Acetobacter pasteurianus* is *Acetobacter pasteurianus* strain AAB5 16S ribosomal RNA gene.

DETAILED DESCRIPTION OF THE INVENTION

With reference to the accompanying figures, there is disclosed a pharmaceutical composition for health improvement, the pharmaceutical composition comprises active ingredient and is prepared from extract of *Acetobacter pasteurianus* when grows on fig.

More importantly, the composition of the present invention is antiviral, antibacterial, and anticancer.

The patient was very weak, there is no desire to eat, vomiting often, cannot stand and walk, nervous, does not like to speak. However, after 24 hours of taking this product, it would be clear that there is a slight improvement on the status of the patient, where the patient gradually begins to eat a little food, as begins to speak more than before. Then after three days of treatment, the patient would start eating even more and becomes more active. Then after several days, the patient would start walking again without assistance, eat more, and becomes more relaxed and less nervous. Furthermore, blood and urine test results were better and sometimes normal, and radiographs showed that the spread of tumors slowed down gradually. The results obtained by treating cancer patients using this product were compared with the ones obtained by treating them using chemotherapy. The results showed that patients who were treated by this product cured in higher and faster rates comparing to the ones who were treated using chemotherapy.

Drinking the pharmaceutical composition does not cause a pain, but it also helps in normal increasing the number of blood platelets as well as hemoglobin ratio, and treats white blood cells which are high-levels.

Tests also showed that taking this pharmaceutical composition returns blood components to normal levels, it is more effective than chemotherapy and radiotherapy.

The majority of the experiments were performed on patients who are hopeless from their lives. However, the improvement was seen within days of treatment and some of them were cured.

The color of the product is yellowish often. pH is between 3.5 and 4, and the weight of 1 ml is 1.09 g approximately. The product is taken orally or by intramuscular injection. It must be filtered and reinforced with serum of Sodium Chloride until pH becomes larger than 4.5 while with intravenous injection it must be reinforced with a serum of Sodium Chloride until ph becomes larger than 6.

Figure 16A:
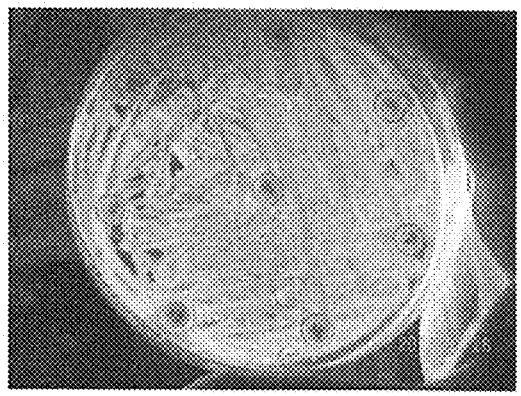
FIGS. 16A through 16C: illustrates Bacteria cause disease resistant to antibiotics.
Figure 16B:
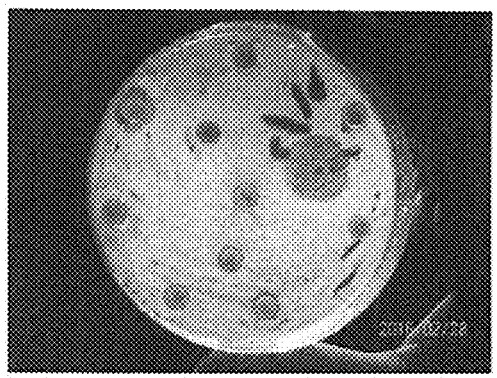
Figure 16C:
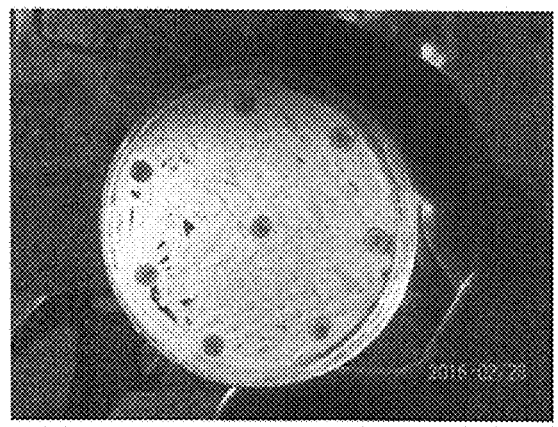
Figure 17:
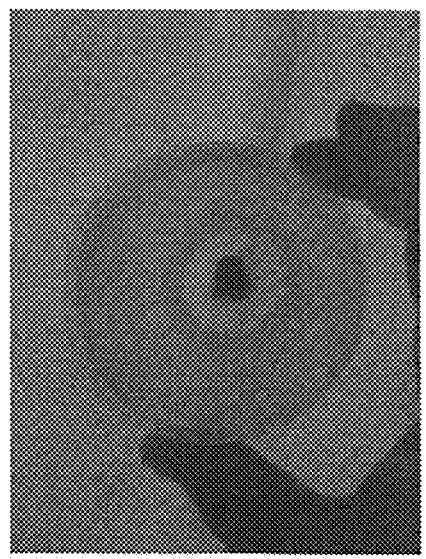
FIG. 17: illustrates the product kills the bacteria that cause disease.
Figure 18A:
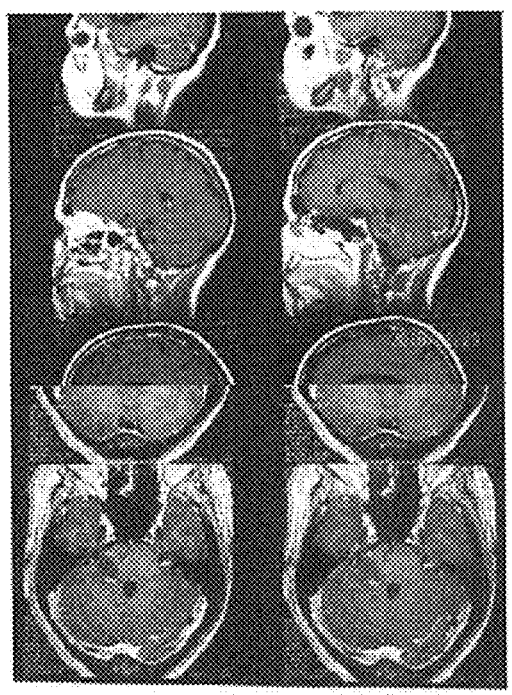
FIGS. 18A through 18D: illustrates several sections of the brain by M.R.I. and a mass in the right middle cerebellum and Multiple Sclerosis by before treatment and report of M.R.I (ABIR).
Figure 18B:
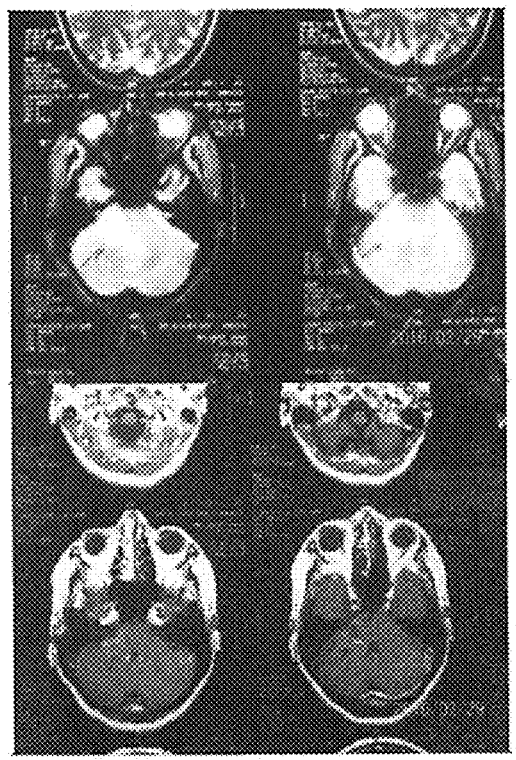
Figure 18C:
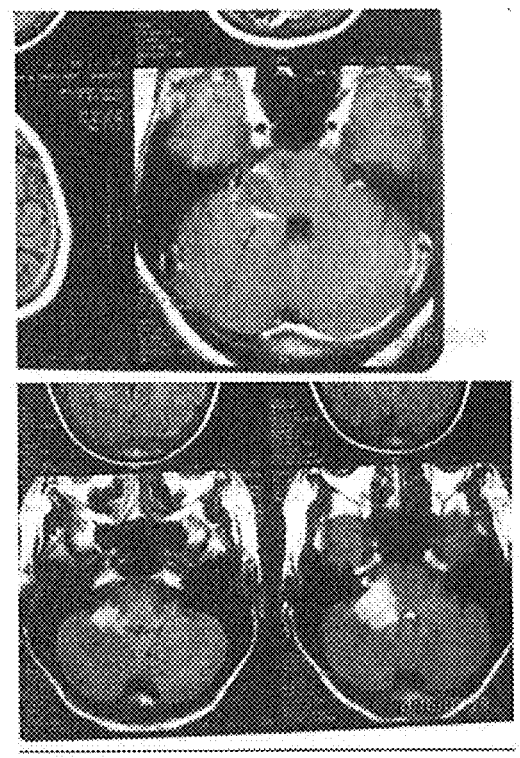
Figure 18D:
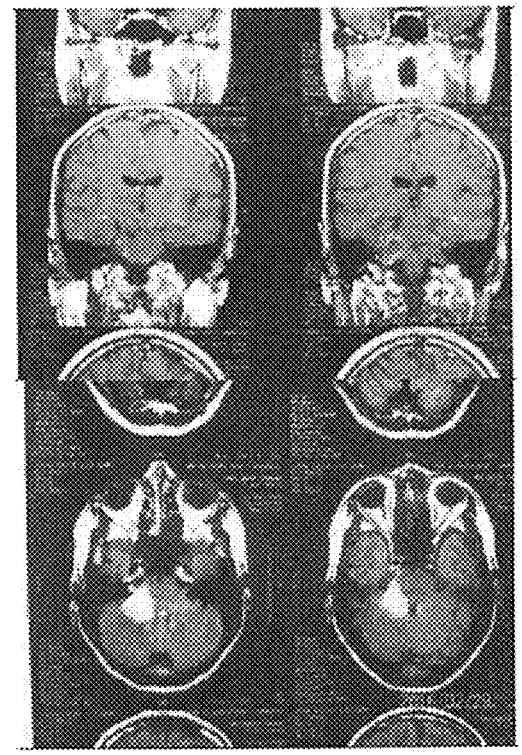
Figure 19A:
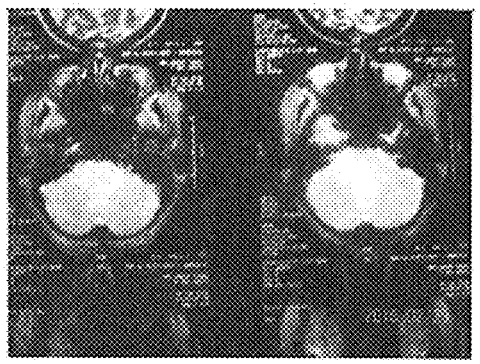
FIGS. 19A through 19D: illustrates several sections of the brain by M.R.I. and the mass in the right middle cerebellum became smaller after 70 days treatment and report of M.R.I (ABIR).
Figure 19B:
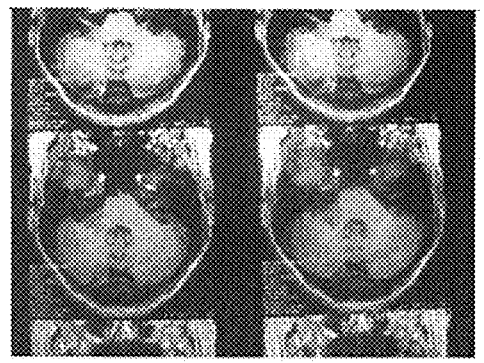
Figure 19C:
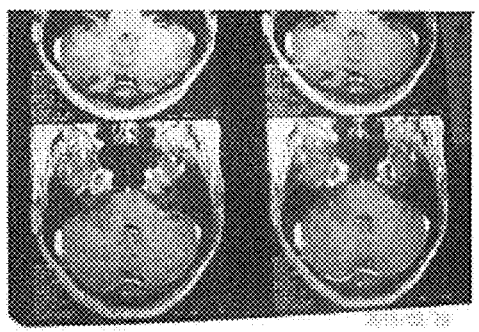
Figure 19C:
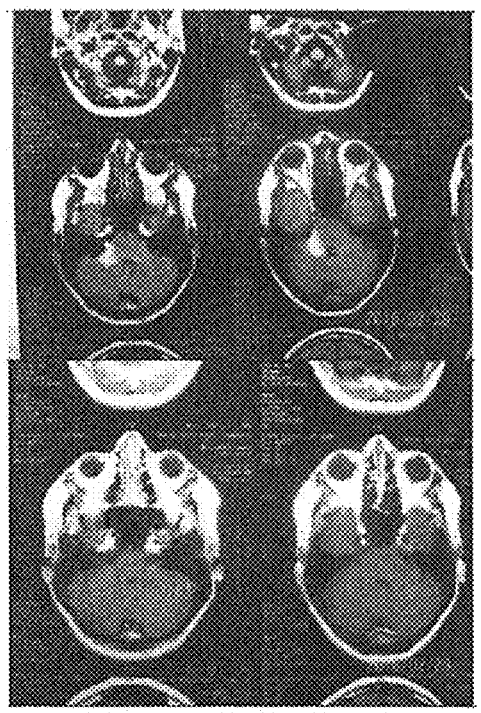
Figure 19D:
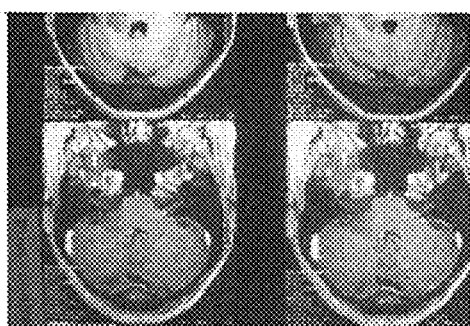
Figure 19D:
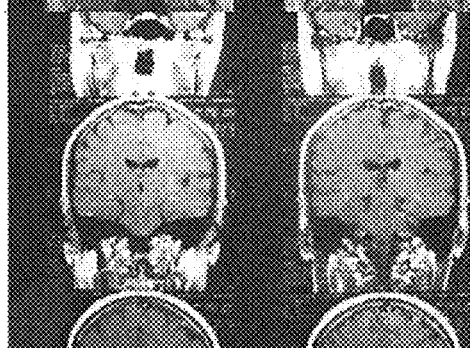
Figure 19D:
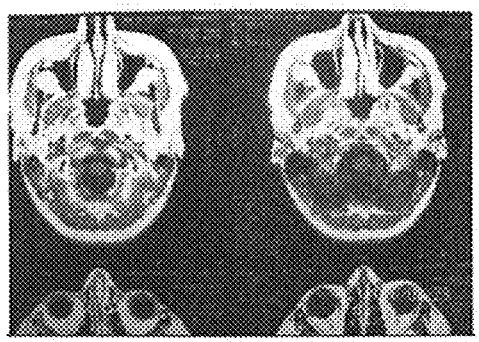
Figure 20:
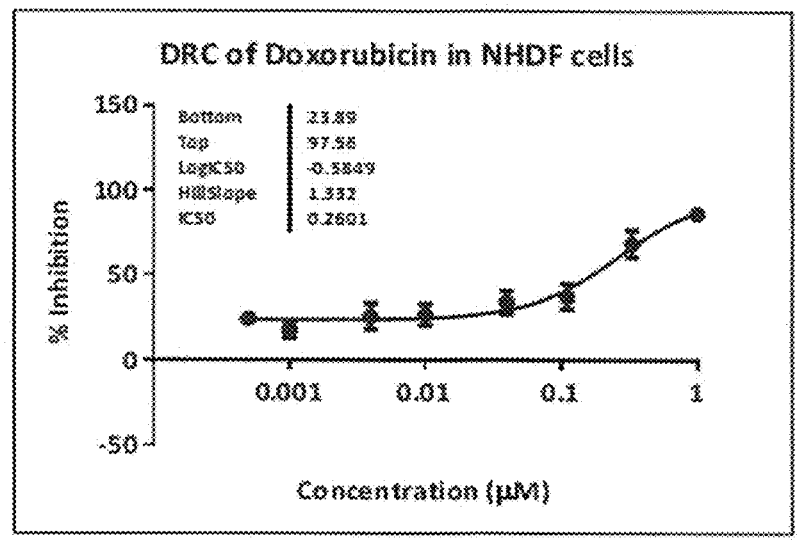
FIG. 20: is a graph showing the effect of doxorubicin on proliferation of normal human dermal fibroblast (NHDF) cells.
Figure 21:
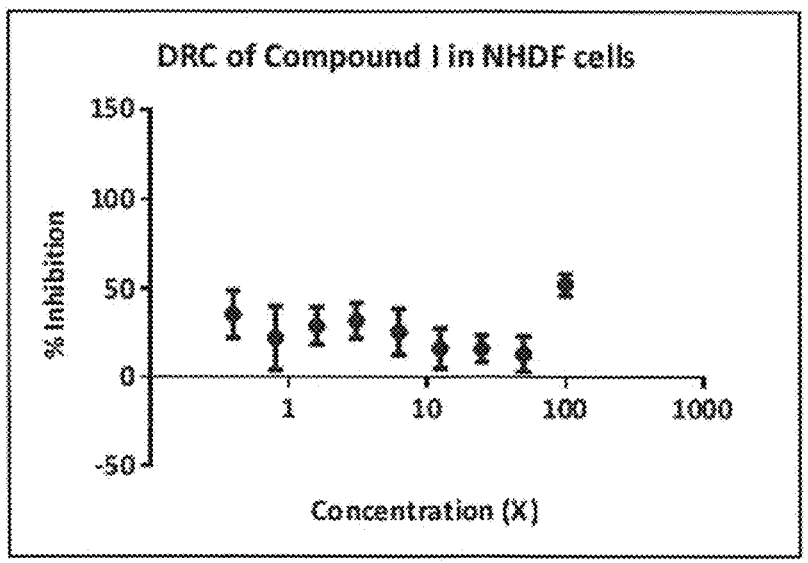
FIG. 21: is a graph showing the effect of one compound on proliferation of NHDF cells.
Figure 22:
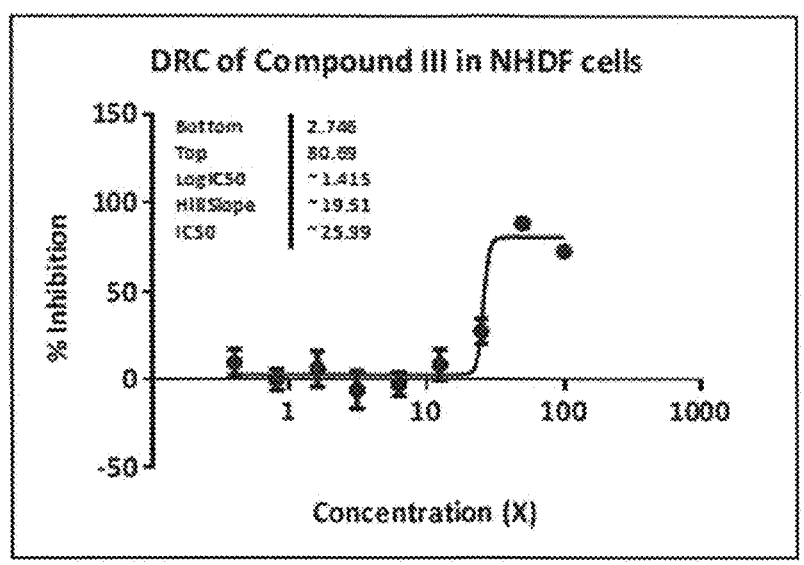
FIG. 22: is a graph showing the effect of another compound on proliferation of NHDF cells.
Figure 23:
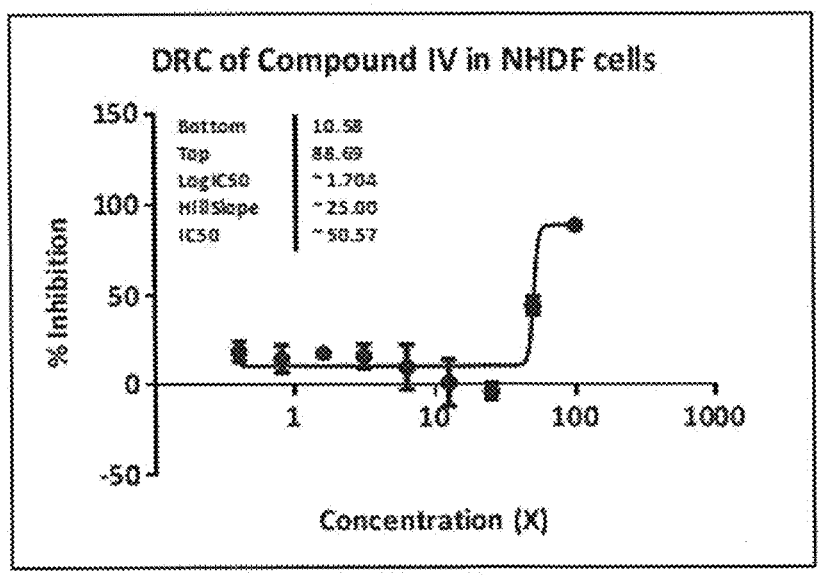
FIG. 23: is a graph showing the effect of yet another compound on proliferation of NHDF cells.
Figure 24:
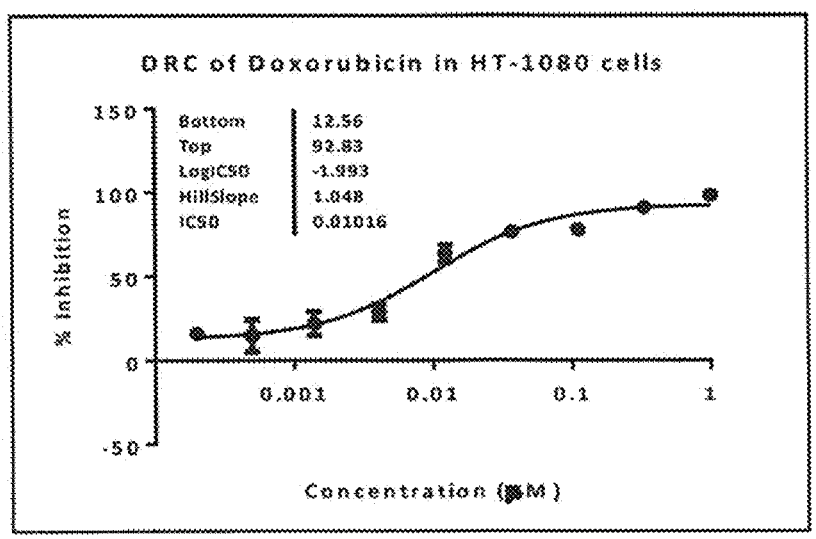
FIG. 24: is a graph showing the effect of doxorubicin on proliferation of HT-1080 cells (a type of fibrosarcoma cells).
Figure 25:
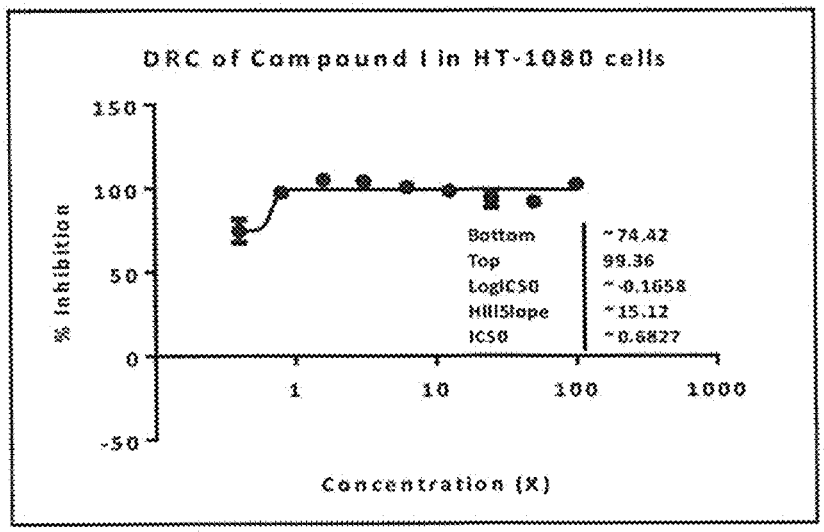
FIG. 25: is a graph showing the effect of one compound on proliferation of HT-1080 cells.
Figure 26:
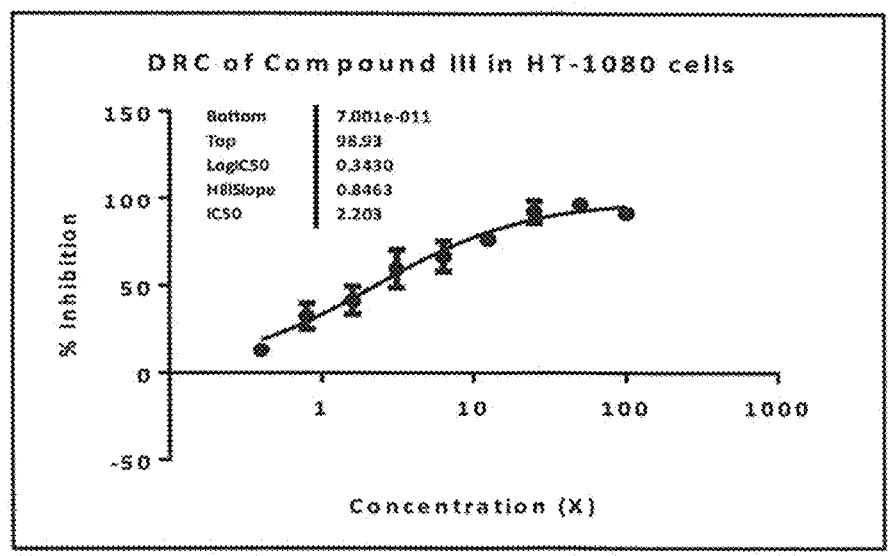
FIG. 26: is a graph showing the effect of another compound on proliferation of HT-1080 cells.
Figure 27:
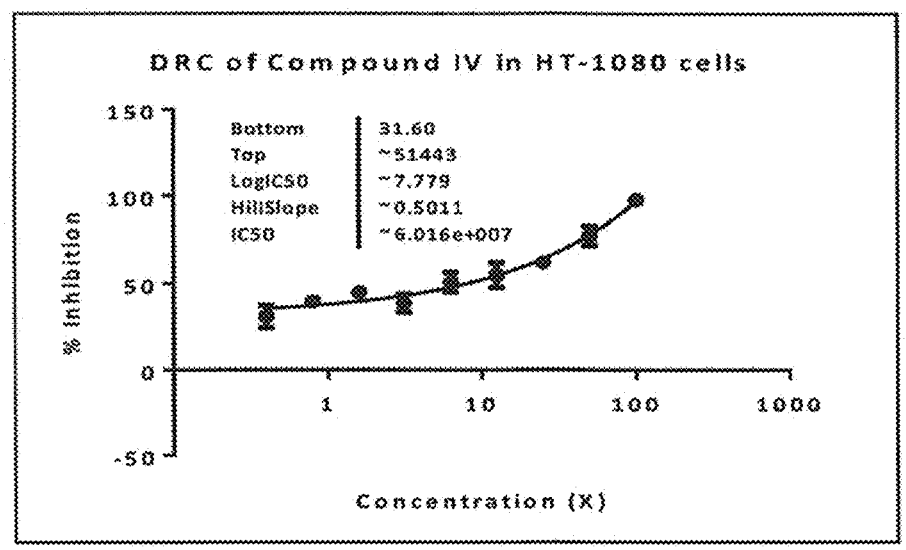
FIG. 27: is a graph showing the effect of yet another compound on proliferation of HT-1080 cells.

When making antibiotic sensitivity test by disc diffusion for a microbial pathogen was obtained it from a sick animal, the zone around a piece of cotton was saturated with this product was larger than the zones around 35 tablets of well-known different antibiotics as illustrated in FIGS. 16 and 17.

It confirms that this product is stronger and better than those antibiotics. The safety of this drug more than other drugs will be clarified later). Can't get powder from the product (extract the efficient substance in the form of powder) because freeze-dry of the product leads to the formation of a very solid and highly viscous material.

The preferred Dosage interval is within 24 hours for 4 days:

Preferably dosage for Birds: Intramuscular injection of 0.5 ml for each 1 kg. With drinking water, 3 ml for each liter of water.

Preferably, dosage for Sheep and cows: Intramuscular or intravenous injection of 1-2 ml for each 10 kg. Orally, 3-5 ml for each 10 kg.

Preferably, dosage for Adult humans: 50-100 ml orally 5 times.

Preferably, dosage for Children: 5 ml orally 5 times.

This pharmaceutical composition has been tested in treating incurable diseases or diseases which are hard to treat. A high rate of healing was achieved with sick birds and animals whose disease have been diagnosed in laboratories. Studies and experiments have been conducted on a groups in which each group contains 10 birds or animals.

Preferably, the pharmaceutical composition comprises *Acetobacter pasteurianus* strain AAB5.

Example 1

Newcastle Disease Test

Newcastle disease is an incurable viral disease. It is the most dangerous disease. The poultry farm containing 5,000 birds, when birds become 20 days old, appeared to Newcastle symptoms: green diarrhea, and descent mucosa liquid from the mouth, swelling in the head, and swelling in the eye. So when did an autopsy on some dead birds found bleeding between the stomach and the stomach glandular mucosa and two ends of cecum became great.

A number of dead birds is increasing from 5 birds per day up to 130 birds during the four days.

100 sick birds were isolated, showing symptoms of the disease in a place outside the farm, and put 10 birds in each group and began to treat these birds with injection half ml (0.5 ml) of natural product within the chest muscles, and 3 ml per liter of drinking water for four days, in the 30 second day of treatment the improvement was clear, where the birds began to eat, the movement has become better, edema of the head became less, and diarrhea less. The cure rate was ranging from 6/10 until it got to 9/10. The rest of the birds of the farm took a vaccine Clone (Clone type of Newcastle vaccines) with drinking water, the mortality rate began to decline until it reached after five days to 5 birds per day, because the birds gained immunity from the vaccine against the disease.

Example 2

Sheep Pox

An experiment was performed on four herds of sheep who suffered from high temperature (42° C.), as well as running nose, watery eye, the lesions were on the face, buttocks and thighs from the inside, as well as on the chest and abdomen.

In each herd, 10 sick sheep took this product after isolating them, the remaining of sheep in each herd took a smallpox vaccine. The sheep that were treated with the vaccine gained immunity against the disease. The 10 sheep were treated by injecting them with 1 ml/10 kg in the buttock, or under skin besides treating them with 2 ml dose orally two to three times daily for four days. Sheep showed signs of gradual improvement and 70% to 90% of them were cured.

Example 3

Foot and Mouth Disease

An experiment was performed at three sheep farms. Sheep suffered from limping, sore gums, and high temperature (41.5° C.). Furthermore, lambs died abruptly after 3 to 5 hours of suckling. Autopsy of dead animals showed white and gray lines on their hearts which is a sign of the disease. The treated 10 sick sheep from each farm with this product after isolating them and the remaining of the herd were treated by the vaccine.

The sheep that were treated with the vaccine gained immunity against the disease. The 10 sick sheep were treated by injecting them with 2 ml in the buttock or under skin besides treating them with 3 ml dose orally twice daily. Sheep showed signs of gradual improvement and 60% to 80% of them were cured.

Example 4

Avian Pox Disease

An experiment was done at 30 poultry farms that were infected by Avian pox. The pimples was appearing on the faces of birds. 10 birds were isolated from each farm and were treated by injecting 0.5 ml in chest and mixing 3 ml per one liter of drinking water. After two days, the birds had much better health, and the pimples disappear on the faces of birds which were active and started eating again. Non-ill birds were treated them with Avian pox vaccine, the birds gained immunity against the disease. In general, more than 70% of the treated birds were cured, but the ones which were not treated died.

Example 5

Mycoplasma Disease

The experiment was at four sheep farms. The sheep suffered from cough and high temperature (42° C.). When performing autopsy on dead sheep, the congestion in the lungs was clear. Three sheep were treated with Ampicillin, but they were not cured. Ampicillin does not affect mycoplasma because mycoplasma does not have a cell wall. Ampicillin only affects the cell wall.

10 sick sheep were isolated from each farm and treated them with this product by injecting them with 5 ml in the buttock or under skin, added treating them with 10 ml dose orally for four days. Another 10 sick sheep from each farm were isolated and treated with 5 ml of Tylosin and Enrofloxacin.

Example 6

Viral Hepatitis

Patients had taken the product, patients have Viral Hepatitis. AST, ALT and bilirubin were high.

Two patients have liquid around liver. they were drinking 500 ml in the day for 15 days AST, ALT and Bilirubin were less from the last test. The liquid around liver was less and the patients became better.

Example: Patient: SHAZA SAMIN. 30 years old, the symptoms of anaphylactic reaction which included:

red skin, edema of the face and neck, dyspnea and chill.

BP: 80/40 mm Hg. The patient was taking 50 mg Diclofenac Sodium every day.

Treatment was managed: Dexamethasone 16 mg and Dimenhydrinate tab.

During the first 24 hours, the general condition almost improved.

After 3 days, the body temperature was sub fibril and started experiencing fatigue. The antibiotic/Amoxiclave and Paracetamol were taken.

But the suffering was been from jaundice and yellowish sclera, the urine became dark yellow.

After two weeks, the blood test showed an increase in hepatic ferments which indicated to hepatitis. The patient was tired, Liver and spleen were senior so her. The test of Viral hepatitis markers showed that the sick has hepatitis A virus and hepatitis C virus.

The patient started taking the natural product, 1 Liter/day for one month. After 12 days the test of AST, ALT, and bilirubin were better from the last test and size of liver and spleen were normal. the patient was very well. A new test in the other laboratory had done because this disease is serious, after a week of drinking the product, the improvement was obvious. Hepatitis C-type was negative.

After a month and a half of treatment, the test results showed improvement in the liver function. SHAZA SAMIN See below tables A through C which show medical report, viral hepatits markers+increase AST, ALT and bilirubin (SHAZA).

TABLE A

Hematology of
Cell Blood Count (CBC)
Sysmex XT-1800

White Blood Cells (WBC)

| | | | | | |
|---|---|---|---|---|---|
| WBC Count | 5150 | 4000-11000 | Cells/uL | 5230 | 2 May 2009 |
| Neutrophils % | 31.1 | | % | 51 | 2 May 2009 |
| Lymphocytes % | 58.4 | | % | 38 | 2 May 2009 |
| Monocytes % | 9.1 | | % | 8 | 2 May 2009 |
| Eosinoohils % | 1.2 | | % | 2 | 2 May 2009 |
| Basophils % | 0.2 | | % | 1 | 2 May 2009 |
| Neutrophils Count | 1600 L | 1800-7700 | Cells/uL | 2690 | 2 May 2009 |
| Lymphocytes Count | 3010 | 1000-4800 | Cells/uL | 1980 | 2 May 2009 |
| Monocytes Count | 470 | 200-950 | Cells/uL | 430 | 2 May 2009 |
| Eosinophils Count | 60 | up to 700 | Cells/uL | 100 | 2 May 2009 |
| Basophils Count | 10 | up to 200 | Cells/uL | 30 | 2 May 2009 |

Red Blood Cells (RBC)

| | | | | | |
|---|---|---|---|---|---|
| RBC Count | 4.00 | 3.8-5.1 | 10^6 Cells/uL | 4.35 | 30 Oct. 2010 |
| Hemoglobin (Hb) | 12.4 | 11.7-14.5 | g/dL | 14.0 | 30 Oct. 2010 |
| Hematocrit (Hct) | 36 | 35-45 | % | 39 | 30 Oct. 2010 |
| MeanRBCVolume(MCV) | 89.5 | 81-100 | fL | 89.9 | 30 Oct. 2010 |
| MeanRBCHb(MCH) | 31 | 26-36 | pg | 32.2 | 30 Oct. 2010 |
| MeanRBCHbConc(MCHC) | 34.6 | 32-36 | g/dL | 35.8 | 30 Oct. 2010 |
| RBCDistributionWidth-CV | 14.2 | 11.6-14.8 | % | 12.5 | 30 Oct. 2010 |
| RDW-SD | 45.4 | 36.4-46.3 | fL | 40.3 | 30 Oct. 2010 |

Platelets (PLT)

| | | | |
|---|---|---|---|
| Platelets Count | 289 | 150-450 | ×1000/uL |
| Plateletcrit (PCT) | 0.31 | 0.17-0.35 | % |
| MeanPltVolume(MPV) | 10.8 | 9.4-12.3 | fL |
| PltDistributionWidth(PDW) | 13.4 | 9-17 | fL |
| PltLargeCellRatio(P-LCR) | 32.2 | 13-43 | % |

TABLE B

Hemostatis, Biochemistry, Trace Metals and Ions and Endocrinology.

Prothrombin Time (PT)
Sysmex CA-1500 by Siemens

| | | |
|---|---|---|
| Time | 11.0 | sec |
| Percent Activity | 98.7 | % |
| INR | 1.01 | Index |
| Control | 10.9 | sec |

BIOCHEMISTRY

| | | | |
|---|---|---|---|
| Alanine Aminotransferase (ALT/SGPT) | 350 H | up to 33 | U/L |
| Aspartate Aminotransferase (AST/SGOT) | 96 H | up to 32 | U/L |

TABLE B-continued

Hemostatis, Biochemistry, Trace Metals and Ions and Endocrinology.

Bilirubin

| | | | |
|---|---|---|---|
| Total Bilirubin | 3.54 H | up to 1 | mg/dl |
| Direct bilirubin | 2.65 H | up in 0.25 | mg/dl |
| Indirect bilirubin | 0.89 H | up to 0.75 | mg/dl |

TRACE METALS & IONS

| | | | | | |
|---|---|---|---|---|---|
| Calcium (Ca) in Serum | 9.2 | 8.5-10.5 | mg/dl | 9.8 | Oct. 30, 2010 |

ENDOCRINOLOGY

| | | | | | |
|---|---|---|---|---|---|
| Thyroid Stimulating Hormone (TSH) Roche Modular E170. | 3.30 | 0.27-4.20 | uIU/ml | 5.66 | H Sept. 17, 2015 |

TABLE C

Viral Hepatitis Markers.

| | | | |
|---|---|---|---|
| Hepatitis A Virus IgM Ab (Anti HAV IgM Ab ECLIA) Roche Cobas e411. Electrechemi luminescene immunoassay. | 7.09 (Positive) | Negative: up to 1.0 Positive: more than 1.0 | IndexVaue |
| Hepatitis B Virus Surface Ag (HBs Ag Elisa) | 0.734 (Negative) | Negative: up to 0.900 Equivocal: 0.900-1.000 Positive: more than 1.000 | Index |
| Second Generation Assay. Hepatitis C Virus Ab (Anti HCV Ab ECLIA) | 8.79 (Positive) | Negative up to 0.9 Equivocal: 0.9-1.0 Positive: more than 1.0 | Index |

Note:
Confirmed on Dec. 16, 2015 = 9.32 (Positive)
Roche E. 170 Modular

Example 7

Antibacterial Activity

As for bacterial diseases whose causes include mycoplasma, *E-coli Pasteurella, streptococcus, staphylococcus,* and *salmonella,* they were treated. The rate of healing is between 7/10 to 10/10. Rate of healing *Brucella* with sheep is 8/10. Rate of healing Mastitis is between 9/10 to 10/10.

*Pasteurella* Disease

*Pasteurella* can be detected via blood test or through symptoms such as running nose, fast breathing, high temperature (42° C.) and high rate of mortality.

The experiment was performed on two groups of 10 sheep each. The first group was treated with this product by injecting them with 5 ml in the buttock or under skin besides treating them with 10 ml dose orally. The sheep showed improvement from the second day and after four days of treatment all the sheep recovered from the disease. The second group was treated with Oxytetraciclin and Enrofloccicln but the improvement was slower than in the first group. This experiment was conducted five times and the same results were found.

*Salmonella* Disease

The experiment was performed at four sheep farms. The newly born lambs suffered from diarrhea and high temperature (41.5° C.) and high level of mortality. Blood tests were performed and found that they were infected with *Salmonella*. 10 sick lambs were isolated and treated with this product by injecting them with 1 ml in the buttock or under skin besides treating them with 2 ml dose orally for four days. The remaining lambs were treated by Oxytetracicline (1 ml injection) and Enrofloxacin (2 ml) and Sulphadiazin mixed with Traimetheroprym. Results showed that the lambs that were treated with the new product recovered faster than the second group. This experiment was ran on three farms and the curing rate ranged from 90% to 100%.

*Brucella* Disease

The experiment was performed on 10 male sheep (Rams) and the infection was confirmed via blood test as well as other symptoms such as high temperature (42° C.), loss of appetite, body weakness and testicles enlargement. The sheep was treated with this product by injecting them with 10 ml in the buttock or under skin for 10 days and they showed signs of gradual improvement until they fully cured after 50 days.

*E-coli* Disease

The experiment was done on the 100 chicks that showed the symptoms of *E-coli*. The birds were treated by mixing this product with their drinking water (4 ml/liter of drinking water) for four days and the chicks recovered.

*Streptococcus*

Bacteria were isolated from cow's milk, where germs were cultured in a lab setting. In the first experiment the germs were treated with this product and all the germs were killed. In the second experiment, the germs were treated with antibiotics including neomycin, streptomycin, penicillin, Oxytetracycline, amikacin, cloxacillin, erythromycin, cephalexin, ampicillin, Spiramycin, enrofloxacin, gentamicin, ciprofloxacin and Tylozin. Results showed that not all germs were killed by any of these antibiotics.

Example 8

Anticancer Activity

There was a benign tumor in the udder which led to a partial or total shutdown of the milk canal. This drug was injected inside the udder which resulted in the disappearance of the tumor. The rate of cure in other cows was 7/10 to 8/10. This result was encouraging to test this pharmaceutical composition for treating cancer.

The patients had done an ultrasound image, blood tests, and a medical report before starting the treatment. One month after the treatment, the tumor is shrinking according to ultrasound image, the blood tests were normal, and medical report. The cancer patients were fatigued, some of them were unable to leave bed, lack of appetite, weakness, and vomiting sometimes. A decrease in hemoglobin, and decrease in Platelets. After 3 days of treatment, the patient's appetite increases, pain disappears, vomiting stops, and the patient feels comfortable physically and psychologically. After a while, his weight increases.

IC50

TABLE 1 shows the results of vitality of the cancer cells of human beings (the genealogy; the genealogy; breed/race FMC-7) that were treated by different concentrations of leachate of the natural product by means of the technique of cells outflow measurement by means of TO-PRO-3.

| % live | % dead | Concentration/time |
|--------|--------|--------------------|
| 91.13  | 8.64   | con                |
| 85.79  | 17.31  | 2μ-24 h            |
| 80.36  | 19.58  | 5μ-24 h            |
| 58.12  | 42.01  | 10μ-24 h           |
| 54.78  | 45.31  | 20μ-24 h           |
| 72.66  | 27.38  | 2μ-24 h            |
| 67.23  | 32.79  | 5μ-24 h            |
| 49.09  | 51     | 10μ-24 h           |
| 39.88  | 60.13  | 20μ-24 h           |
| 7.28   | 92.72  | 200μ-24 h          |

The concentration that caused death to 50% of the cells (IC50) was measured through; depending on the following equation;

$$50\%\text{-Low ln }h\%/(\text{High ln }h\%\text{-Low ln }h\%)\times(\text{High Conc-LowConc})=IC50.$$ rule:

It was revealed that it equals:

IC50=14.44 μL/ml (when treatment for 48 h)

IC50=22.72 μL/ml (when treatment for 24 h)

Testing the effect of the extract of the natural product on both the viability and the proliferation of both the stimulated and non stimulated lymphocytes of the human blood.

| With phyto 24 h | | No Phyto 24 h | | |
|---|---|---|---|---|
| % Live | % Dead Cells | % Live | % Dead Cells | Concentration |
| 88.08 | 11.97 | 99.72 | 0.28 | Control |
| 84.73 | 15.32 | 99.40 | 0.60 | 2µ |
| 83.53 | 16.50 | 99.73 | 0.27 | 5µ |
| 82.42 | 17.63 | 99.68 | 0.33 | 10µ |
| 79.15 | 20.79 | 98.35 | 1.67 | 20µ |
| With phyto 48 h | | No Phyto 48 h | | |
| % Live | % dead cells | % Live | % Dead Cells | Concentration |
| 68.46 | 29.74 | 96.91 | 3.02 | Control |
| 70.30 | 28.59 | 96.94 | 3.02 | 2µ |
| 73.95 | 24.72 | 97.06 | 2.88 | 5µ |
| 67.32 | 31.25 | 96.90 | 3.03 | 10µ |
| 42.17 | 55.37 | 86.39 | 13.67 | 20µ |

*phyto = phytohemagglutinin

From the above Table, the calculation the IC50 of both the stimulated and non stimulated lymphocytes to be divided by the effect of the phytohemagglutinin.

| $IC_{50}$ | | | |
|---|---|---|---|
| With phyto | | No Phyto | |
| 24 h | 48 h | 24 h | 48 h |
| 116.12 | 16.39 | 833.03 | 81.40 |

MTT Analyse for Human Liver Carcinoma Cells

About 93.4% of the human liver carcinoma cells were inhibited after 48 h treatment with 100 ul of the product, while 70.87% of cells were inhibited at 6.25 ul of the product at the same time point.

Raw Data and Data Analysis:

| | OD | Mean | SD | Cell |
|---|---|---|---|---|
| Control (Cells only) | 1.5742 | 1.5190 | 0.0986 | 100.00 |
| Sample: - | 1.5776 | | | |
| Sample Concentration 1 | 0.0996 | 0.1001 | 0.0009 | 6.59 |
| | 0.0996 | | | |
| Sample Concentration 2 | 0.1073 | 0.1067 | 0.0028 | 7.03 |
| Sample: | 0.1092 | | | |
| Sample Concentration 3 | 0.2646 | 0.2567 | 0.0069 | 16.90 |
| Sample: | 0.2518 | | | |
| Sample Concentration 4 | 0.3120 | 0.3135 | 0.0085 | 20.64 |
| Sample: | 0.3058 | | | |
| Sample Concentration 5 | 0.5347 | 0.4425 | 0.0853 | 29.13 |
| Sample: 6.250 ul | 0.3665 | | | |
| Sample Concentration 6 | 1.0409 | 1.1085 | 0.1406 | 72.98 |
| Sample: 3.125 ul | 1.0145 | | | |
| Sample Concentration 7 | 1.5978 | 1.5852 | 0.0561 | 104.36 |
| Sample: 1.563 ul | 1.5239 | | | |

Protocol:
1. 5,000 cells were seeded per well and incubated at 37° C. and 5% $CO_2$ for 24 hours.
2. Culture media was aspirated from each well, and cells were incubated with sample for 48 hours.
3. 15 ul of MTT solution was added per well and incubated at 37° C. and 5% $CO_2$ for 4 hours.
4. 100 ul of 10% SDS solution was added per well and further incubated at 37° C. and 5% $CO_2$ overnight.
5. Absorbance value was recorded at 575 nm.

Notes:
HepG2 cells (human liver carcinoma cells) used in the experiment were not subjected to any cell culture contamination screening to detect mycoplasma, bacteria and fungi.

| IC50 | 5.040 ul |
|---|---|

GraphPad Prism 6 software was used to construct the graph and calculate the IC50 It is best that the product is a liquid for analyses MTT (non freeze-dry)

Breast Cancer 13 women took this product for treatment. One of them did not take any chemo or radio therapy previously. The size of the tumor was 3.5 cm. After one month of treatment, it became 2.8 cm. 6 months later, the tumor disappeared completely. As for the rest of women, the size of tumor before treatment was 2.5 cm to 4 cm. After one month of treatment, tumor shrank with rate 0.5-0.8. 3 months later, 3 women scanned the tumor. The result was that the tumor had shrunk for 1.2 cm to 1.5 cm.

Example

Wasfyia a female patient 55 years old, The patient was suffering ductal carcinoma NOS Type invasive grade 3 invasive. The X-ray study, ultrasound and CT-scan showed the size of tumor, it was 3.4 cm×3.2 cm×2.7 cm in the left breast and close to the nipple. The edges of the tumor were irregular and heterogeneous plus enlarged axillary lymph nodes of the left side. The patient started to drink the (natural product) and compresses with the product were applied to the tumor area during the period of treatment. Tumor markers test became normal after 15 days; also the ESR, AST, ALT and Creatinine were normal, suggesting that the natural product is safe. After 11 weeks, the tumor disappeared. The biopsy was taken from axillary nodes, abnormal cells were not detected. Wasfyia lives does not suffer from the pain, does not complain of any defect in the body which is under periodic surveillance.

Rectal Cancer

A man was afflicted with it, and could not evacuate except once a week and with difficulty. The man took the product orally and by an enema. He recovered and started to evacuate every day. One month later, he made an ultrasound image and found that the tumor shrank so much. Two month later, the tumor disappeared.

Ureter Cancer

A man had it, the health improved during treatment, small pieces of tissue came out with urine for several times. The tumor disappeared according to the ultrasound image.

Prostate Cancer

A study was conducted on 15 patients. 5 of them are older than 70 years. They were not able to urinate. They took the product, and their health improved a lot as they became able to urinate easily. While other patients started to recover, and they became able to urinate, and their prostate was not removed. Example: MAHMOUD who suffered from Prostate Cancer (PROSTATIC ADENOCARCINOMA). The CT scan revealed the presence of metastases, Crusty cysts on the kidneys, and thickening of the wall of the stomach, and prostate size of 200 cubic centimeters. It is important to mention here that this person is also a cigarette smoker. CT scan images are attached.

This patient started drinking this product, 100 ml each day. The urination became easier. The taking a new biopsy and test it, the result of biopsy was normal. Look at FIGS. 9-14.

Brain Cancer

The research had on four patients. The symptoms were headache, difficulty in walking, speaking and with sensation. The tumor was appearing on MRI indicating the location of the tumor. Patient was experiencing difficulty in speaking, tingling or numbness in the arms, legs, trunk of the body, or face. She lost sense of the gum and the lip clumsiness, particularly difficulty staying balanced when walking, spatial perception, Vomiting. she has had a mass in the right middle cerebellum and Multiple Sclerosis (FIG. 18). She began drinking the product at 16 Nov. 2015. The health became better after one week. Walking and speaking were better, the sense (feeling) of the gum and lip was return, 70 days of treatment, the mass in cerebellum became smaller, the patient was very well (FIG. 19).

The physician removed a lipoma from a patient's foot. One year later, the lipoma returned, and he removed it. 6 months later, the tumor returned, so he injected the pharmaceutical composition inside the lipoma. Few days later, the tumor started to shrink until it disappeared. This physician injected this pharmaceutical composition in warts once. 21 days later the wart or tumor disappeared from fingers. This experiment was conducted on 30 people. This pharmaceutical composition was tested on different kinds of cancer in lungs, liver, pancreas, oaldm, kidney, intestines, brain, stomach, and uterus. In most cases, cancer was of the fourth degree. Treating this degree is very difficult, but results were excellent as their conditions improved after 3 days of treatment. One month later, the tumor shrank with 25%. Results were better with patients who did not take any chemo or radio therapy.

Anti-Inflammatory Activity

The treatment had done with the pharmaceutical composition for sick animals which disease was so hard to cure. The rate of healing was 80% of these diseases: Encephalitis, Blacklisted disease, and Inflammatory bowel.

Many birds and animals have been slaughtered, the anatomy was after a week, 14 days, 21 days, and 28 days of the last dosage. Kidneys and livers were normal. This proves that this pharmaceutical composition is very safe.

Two Men had H1N1 Flu.

Two men had H1N1 flu, the diagnosis was in the hospital, they took the pharmaceutical composition, they were healed in 3 days. This drug was also tested on patients of respiratory infections and flu. Healing was 100/100 during 2 to 4 days.

Asthma

This experiment was performed among 100 volunteers who suffered from bronchial asthma and had symptoms of asthmatic component. The patients were using inhalers to relief breathing. These patients was taking 70 ml of the product 5 times a day for one month.

90 patients stopped using all the medications that they used to have, for a whole year.

10 patients need to take the product 3-5 days, 70 ml, 5 times a day every 2 months.

There was a typical case of a child 10 years old, who has suffered from asthma since he was two years old. The patient has been suffering from difficulty of breathing and a cough, and often feels suffocated and becomes cyanotic to the point that his father was forced to rush him to the hospital to manage him with oxygen inhalation. He started to take the product by the scheme which prescribed above, and he has been in a good health. He drinks the product 3-5 days every 2 months. These are the pharmaceutical composition that the boy was using:

Ventolin Nebules 2.5 mg solution for inhalation salbutamol sulfat manufactured by GLAXOSMITHLINE. VENTOLIN spray 100 mcg, Flixotide Evohaler 50 mcg manufactured by Glax Welcome Inc. ALECAST 5 mg Montelukast sodium manufactured by Ilko Corp.

The child took two table spoons of the pharmaceutical composition five times daily and starting feeling better after 72 hours and surprisingly, he was fully cured after a month.

Urinary and Genital Inflammation

Treating urinary and genital inflammation (acute and chronic) was studied. The study was conducted on 10 men and 60 women. Some of them had urinary sand with the infection. After taking the product, the times of urination and quantity of urine increased. Backache appeared for two days, then pain disappeared, and the urine color transformed from dark yellow to clear yellow. Healing started after two weeks to a month. Sand disappeared from urine.

Treating inflammatory bowel disease whose cause is viral. It was diagnosed by physicians.

The noticed signs were high temperature, diarrhea, and vomiting. After giving the pharmaceutical composition to children, vomiting stopped within 12-36 hours. Diarrhea decreased to the half, and healing was achieved within 3-4 days.

More than 15 patients with naphtha in tongue and mouth were treated by applying the product on the place of pain and taking the pharmaceutical composition orally. Complete healing is achieved after 3 days.

Skin inflammations and wounds were treated. The experiment was conducted on patients whose wounds are simple by applying the pharmaceutical composition directly on the wound. Within 12 hours, pain and swelling disappeared.

Compresses of product were applied on eczema in the feet of a patient who used many drugs for 3 years but without interest. However, with applying this pharmaceutical composition for 20 days, complete healing was achieved.

The treatment by pharmaceutical composition the was against a psoriasis in the hand.

Two patients with Mediterranean fever were treated. This disease is very challenging.

A large zone was formed around wetted cotton with the product on solid medium (Sabouraud Dextrose Agar) which the *Candida* were cultured.

This product has killed viruses that are stronger than the AIDS virus, for example the Newcastle virus and the swine flu virus. So possible the product kills AIDS virus. For example, fowl box when the product was injected in the sick birds the pimples on their face disappear after 24 hours. A 24-hour treatment for Newcastle disease will lead to disappearance of the green diarrhea, congestion on face, and the mucus liquid that gets out the mouth.

Signs of improvement appear on swine flu patients 24 hours after taking the pharmaceutical formulation.

A small girl had Mediterranean fever. The white cells were 22000/ml. She drank from the pharmaceutical composition at one day and she became very well. She ate and played. on the second day, the number of white cells became 5000/ml in a new report.

Lung cancer patient, the cancer was widespread in the body. The patient was suffering from vomiting after eating any food or drink, but did not vomit the product. Signs of improvement appeared when the product was taken during the two weeks, but when the time came for the chemotherapy, did not drink from the product for fear of drug incompatibility.

Most of the patients after 3 days of the treatment, they got improved and their appetite for food was very good also. They felt energetic. After one month, the tumor shrank 0.5 cm and the blood components were very good and the pain disappeared. Besides, the vomiting ended. Aphta in tongue and mouth: When the patient puts the pharmaceutical composition on the place of pain and drinks the pharmaceutical composition, he feels improved after 24 hours. The pharmaceutical composition is distinguished by its safety for usage. Many patients drank a greater dose of the pharmaceutical composition than the amount, there were not any side effects.

Many birds and animals have been slaughtered for anatomy. After a week of the last dosage, kidneys and livers were normal. Repeating the slaughtering after 2, 3 and 4 weeks proved the same results and that proves that this pharmaceutical composition is safe.

Experiment Animals Two Groups of Rabbits:

5 females rabbits the rabbit his color is brown and white, its number is 5, its weighing is 520 g. It is rabbit No 5. 2.5 gram of freeze-dry of the natural product (it is callous material and very sticky) was taken by the rabbit No 5 at twice after dissolving with the water (each time 1.25 g during 24 hours orally). After two days there no any changes for this rabbit.

The rabbit No 1 (control): its weighing is 420 gram, its color is white, it was put a red color on its back The rabbit No 2: its weighing is 290 gram, its color is white, she took 0.86 gram of freeze-dry product (860 mg) in its mouth, After dissolving it in 4 ml water, she took 1 ml orally each times in 24 hours The rabbit No 3: its weighing is 250 gram its color is white and there is black color around its eyes She took 0.74 gram from freeze-dry product in its mouth after mixed with 4 ml water, she took 1 ml orally each times in 24 hours The rabbit No 4: Its weighing 470 gram, its color is black and white, She took 1.39 g of freeze-dry product after dissolving in 4 ml water, she took 1 ml orally each times in 24 hours.

The rabbits that their numbers are 2, 3, 4, their weighing is 290+250+470=1010 gram, the freeze-dry product is 0.86+0.74+1.39=2.99 gram. On the fourteenth day of taking the product, the rabbits were slaughtered.

Their weighing were: Rabbit number 1 was 610 gram, rabbit number 2 was 520 gram, number 3 was 410 gram, number 4 was 650 gram, number 5 was 760 gram.

The results of tests were very good, and there were not effects for product on liver cells and kidney cells at all rabbits, and the tests were normal.

This pharmaceutical composition is distinguished by its treating many diseases which are caused by viruses and bacteria.

Preferably, This drug takes the form of solution and its results are very good so there is not any pain when used Some Viruses Cause Cancer This scientific fact was clear through this research and invention, which put an end to the deadly disease: cancer.

This natural product treats viral diseases, primarily, it is killing viruses, and has been tested on a lot of viral diseases, and the recovery was within days.

For example, bird's smallpox is a viral disease, these viruses attack the skin cells and cause changes in the lifecycle of these cells and form pimples (blisters) on the skin of the face, when injected with 1 ml of the product in a bird's chest and These sick cells that their life was disrupted by the virus's effect is considered as abnormal by the immune system and is resisted by the immune system after the death of smallpox viruses.

On the second day, the lesions begin to dry out and in a few days the pimples disappear. The viruses that cause cancer attack the nucleus of the cell in the body of the organism and incite the cell nucleus at random infinite divisions. These viruses change the lifecycle in the cells which result in new cells, abnormal, not intact and increase quickly. These cells which were attacked by viruses that cause cancer, and which her name "the mother cells are the ones that originated the formation of the new young abnormal cells.

Viruses live inside the mother cells and those viruses are not necessary present within the new abnormal cells that forms the tumor.

The influx of blood through the capillaries to the new young cells (inside the tumor) is greater than the blood flow to the normal cells. The flowing blood will be circulating from the tumor to the circulatory system, so some viruses could move to a new organ (for example, liver, brain, kidney etc). These viruses attack the nucleus of some cells in a new organ and instigate it to a lot of divisions and multiply and form a new tumor. And thus many viruses is growing within the body which results in the formation of many tumors in different sizes until the cancer reaches the bone, then the patient does not live longer than a few months When the patient begins drinking the natural product, a lot of the viruses that cause cancer die, when the patient continues drinking the product the proportion of the death of these viruses increases. When the natural product enters the body, it begins to kill viruses that cause cancer, then the mother cells lose the viruses which control the DNA of cells and change in the components of the life cycle of the cells, and these cells become weak, the immune system considers these cells strange and begins resisting them, the collaboration between the immune system and natural product's death of cancer cells have been transformed into fibrotic cells (not able to reproduce cells), the tumor remains contracted, and when you take a biopsy from the tumor, the test result is to be found (NO EVIDENCE OF MALIGNANCY).

While chemotherapy kills the abnormal cells in the tumor and part of the healthy cells (normal cells), it does not kill viruses that cause cancer. The cancer cells feed from the blood stream more than healthy cells do. The healthy cells feed and consume the natural product from the blood, but the cancer cells feed in larger amount sand thus consume more of the product from the blood stream. So the product will kill these cells.

When it was performed MIT analysis on liver cells, after 72 hours of the experiment, 100 microliter of product killed 8/100 healthy cells and 92/100 cancer cells.

But using 50 microliter of product killed 0/100 healthy cells and 82/100 cancer cells.

The proportion of the death of healthy cells is very rare and unimportant. These cells died because they took an excessive amount of the product, while cancer cells are programmed by the virus to feed in larger amounts and thus consume more natural product which enters the body like a nourishment, the cancer cells die when they take a large amount of the natural product as food.

The theory that the cause of cancer originates from a cancer cell is wrong. You cannot prove the theory. Example: a woman fell ill with breast cancer and several months later, the new tumor reached the brain. How can a cell of tumor leave the tissue and these are interlinked with each other!? Is it reasonable that the cancer cell of breast moved to the brain that is surrounded by membranes that prevents a lot drugs from reaching the brain? Only small quantities penetrate through membranes! While the idea of moving the virus through the blood to the brain from the breast would be more acceptable.

The viruses are inside the mother cell, but another cells of the tumor does not necessary contain the virus. So the best way to isolate the virus is with examination of all cells of tumor which is uprooted by electronmicroscopy, so there is a need for a large number of researchers to then repeat the experiment on tumors taken from new patients. If the cancer disease was in its beginning, viruses die during the treatment with the product in less than a month, but if the disease is in an advanced stage, it means that viruses are becoming huge in numbers and the mother cells are more, then the patient needs more quantities of the natural product to be enough to kill all viruses.

if the viruses and the bacteria, were seen by eyes, the people cannot walk in the streets because the viruses and the bacteria are too many, but the immune system for the human and animals protects against viruses and bacteria.

Many cancer patients have relatives who were died with this disease. Then concluded that these viruses can be transmitted by parents and grandparents to their children and grandchildren (vertical transmission) and the transmission of the disease is not hereditary, but this transition happens with simple modification. The virus enters the body through the mouth (food and drink), an injury and contaminated instrument. When the virus becomes inside the body, the disease will not happen. Because the immune system is strong. But when the immune system weakens, the virus can form the cancer. But if there's a weakened immune system and the virus is not within the body, cancer will not be formed.

When exposed the experimental animals to radiation, some of them did not get sick with cancer. The cancer happens according to the following equation: specific cancer viruses+weak immune system=cancer.

Also the immune system weakens when the body is exposed to stress factors such as radiation, eating some materials, hormones, chemicals, smoking, frequent hunger for long periods, fatigue, chronic diseases and various stress factors . . . . But without the presence of the virus, cancer will not be formed.

A young man was beaten on his leg, a large tumor constituted in the place of the trauma, the biopsy of the tumor was showed cancer, tissue cells that had been beaten became weak, the virus arrived by the blood to the tissues or from outside the body through the wound, Cancer was in the place of the damaged area.

A lot of people and animals have been beaten and did not get cancer, because the virus did not arrive to the place of trauma.

Lady fell down on the ground, and hit her pelvis, it led to the weakening of the pelvic area and when the virus arrived to pelvis, the cancer constituted in the pelvis Boy was sick, both tonsils were inflamed, he took antibiotic he became better for a period of time and then the cancer formed in the tonsils. The bacteria that attacked the tonsils made it weaken, when the virus arrived to tonsils, cancer formed. But a lot of people get tonsillitis and because of the absence of the virus they do not get cancer. These were some of several cases. Only three cases of cancer have been seen among hundreds of thousands of animals and birds, (tumors inside the belly of the animal).

The vision was after the slaughter of the animal or bird. It is true that viruses were found, but these animals have strong immune systems because these animals were eating plants growing in the nature without human interference. These herbs or plants are not exposed to insecticides or fertilizers or hormones or pesticides that weaken the immune system.

Also noticed that the nomads do not get sick with cancer except a few numbers. Compared between the nomads and the people that live in the cities, the affected by the disease were more in the cities, because the nomads have a strong immune system they rely on eating yogurt, butter, fat, bread, meat, natural plants and there is no population congestion and they breathe fresh air (not polluted).

Concluded from all these observations that keeping the immune system strong and getting away from everything that weakens it (radiation, smoking, chemicals or hormone into the body) is much better than treatments Also noticed that the psychological factor has a role in the progression of the disease, the patient who knows his illness is cancer, his health worsens more than the patient who does not know his illness.

Five olive trees were irrigated with the natural product a few times, and after many months the amount of the olives produced were better than the olive trees that were not irrigated. This natural product is useful for the plants.

This product was tested as a treatment for insect bites by applying it directly to the area of the bite. The pain was gone immediately.

This product was also used for treatment snake bites to newly born animals, the signs of improvements showed gradually until the animals were recovered in three days.

Three people were suffering from Maltese fever drank this product and recovered completely.

Carcinoid

This patient had a tumor at the branch of aortic arch. The tumor was pressing on the superior vena cava and the Brachiocephalic vein at left so caused infarct it. The patient was treated with ENDOXAN-DOXORUBICIN-CARBOPLATIN, three doses, She did not respond to the treatment, but the size of the tumor increased, so a part of the tumor was removed after the pathological examination for the cells of tumor, the result was ATYPICAL CARCINOID TUMOR, There was also a node in front of the trachea and the node down the aorta an several held above his left collarbone and several pulmonary contract and small foci of liver. She was treated with chemotherapy protocol TAXOL 300 mg with Etoposide and remained under surveillance by CT-scan several times, but the tumors became more size, and the tumor spread in the body until it arrives in the entire bone, it was clear by Tc-MDP BONE SCAN. The chemotherapy treatment weaken immunology, then the viruses became stronger and disease grows. The patient was taking ZOMETA 4 mg each month for fixing the calcium on bone. The patient was very poor health (low calcium in the blood—severe anemia in a large—platelets decrease—a large weight loss—severe pain in the bones—a lack of appetite). The patient began to drink natural product at a dose of 500 ml per day the size of the tumor was 99*67*108 mm. The patient within three days of drinking the product her health improved (increase in weight and appetite and hemoglobin and platelet and lime better and activity of the body and finally the demise of the pain), the tumor became 103*67*94 mm.

Preparation of the Composition Form Figs

Figure 1A:
FIGS. 1A and 1B: illustrate an agar plate, *Staphylococcus* growth showing halo around the pieces of figs and pieces of cotton are wet with product.
Figure 1B:
Figure 2A:
FIGS. 2A and 2B: illustrate liver and kidney tissue cells following tests on rabbit No. 1.
Figure 2B:
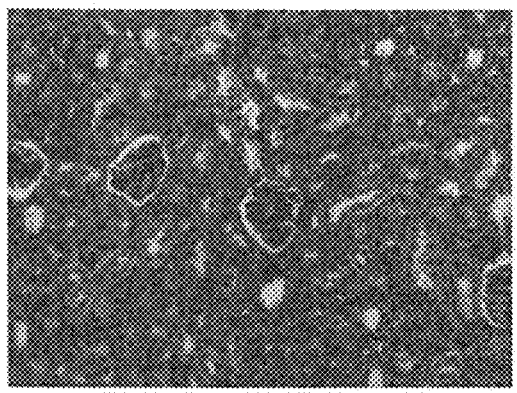
Figure 3A:
FIGS. 3A and 3B: illustrate liver and kidney tissue cells following tests on rabbit No. 2.
Figure 3B:
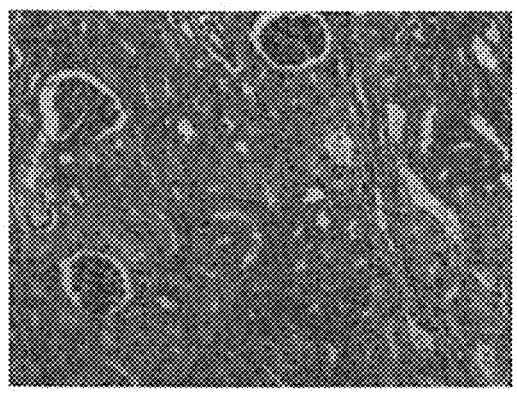
Figure 4A:
FIGS. 4A and 4B: illustrate the liver and kidney tissue cells following tests on rabbit No. 3.
Figure 4B:
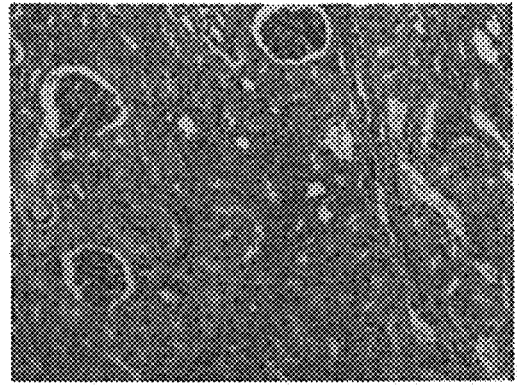
Figure 5A:
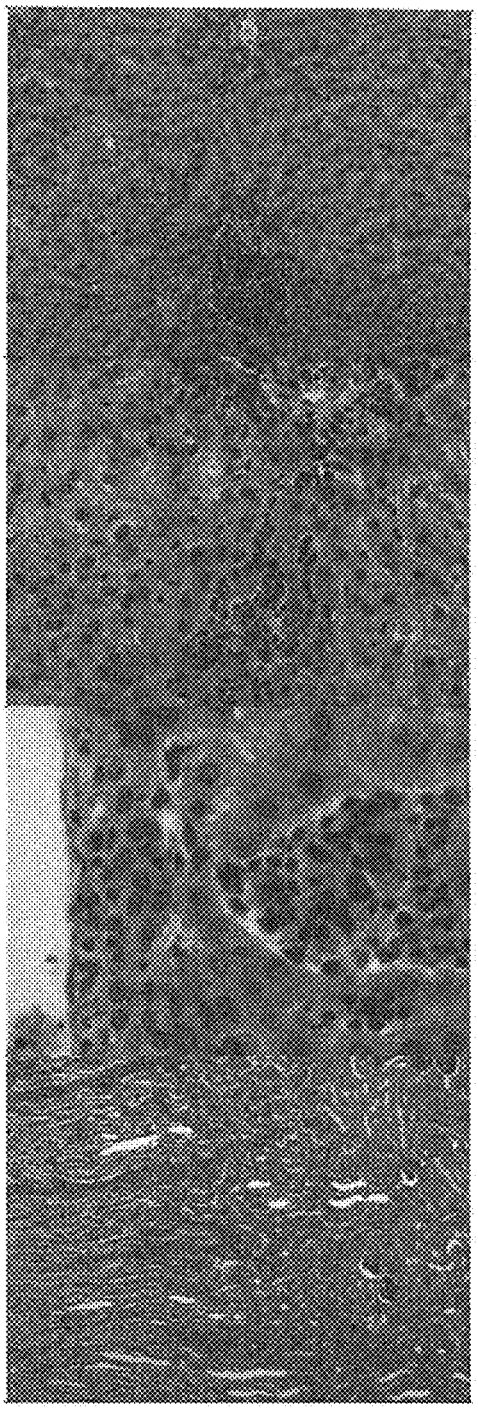
FIGS. 5A and 5B: illustrate liver and kidney tissue cells following tests on rabbit No. 4.
Figure 5B:
Figure 6A:
FIGS. 6A through 6D: illustrate liver and kidney tissue cells following tests on rabbit No. 5.
Figure 6B:
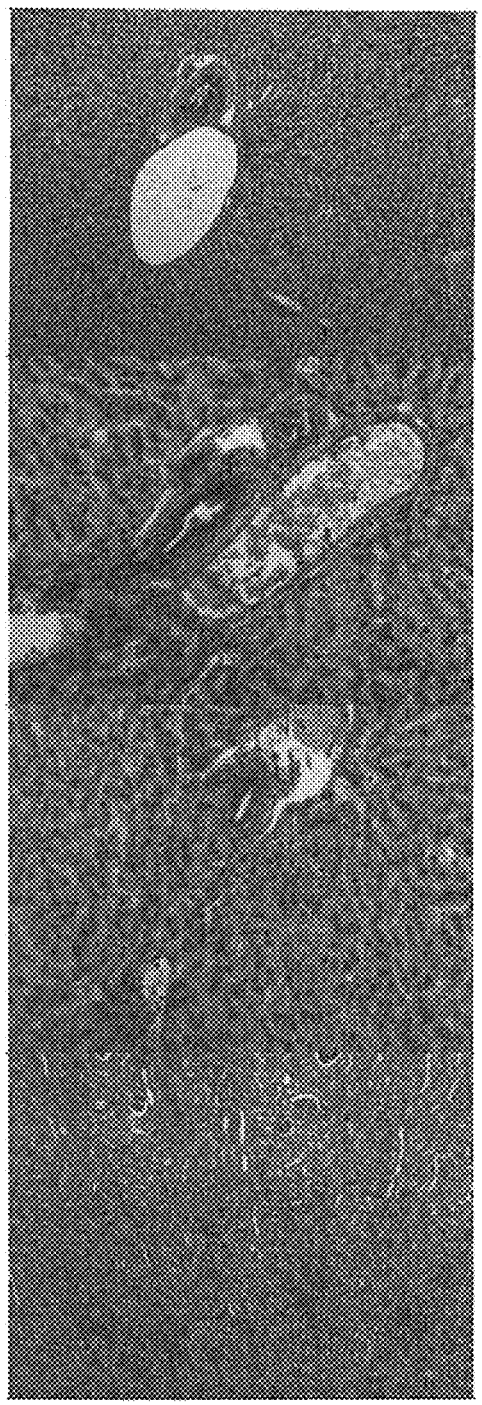
Figure 6C:
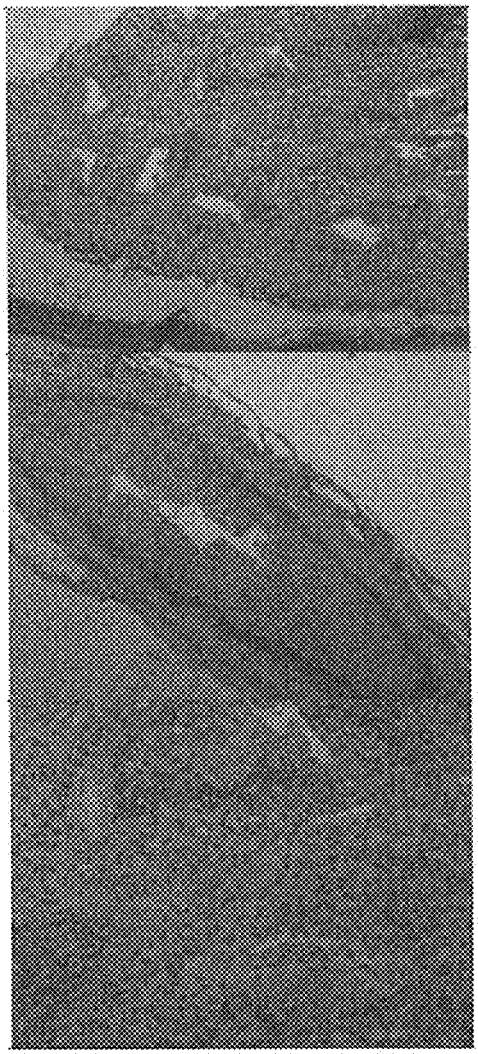
Figure 6D:
Figure 7A:
FIGS. 7A through 7F: illustrate Micrograph microorganisms within natural product (gram).
Figure 7B:
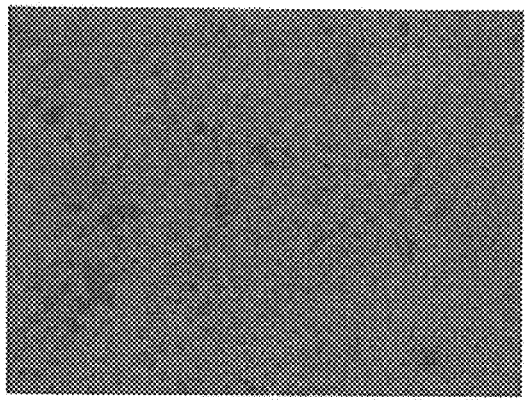
Figure 7C:
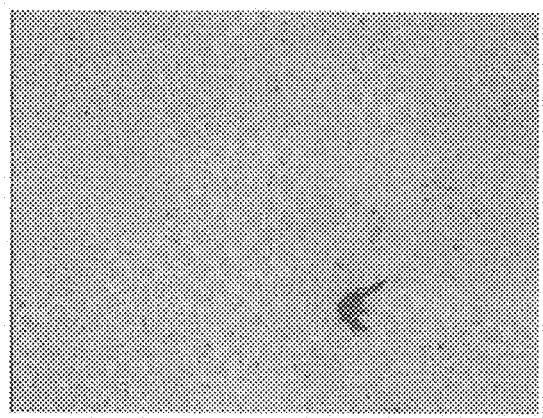
Figure 7D:
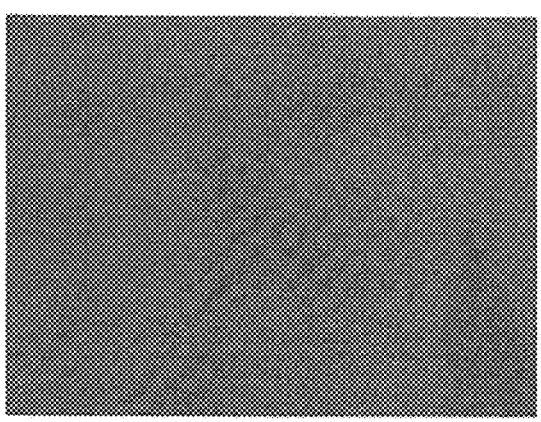
Figure 7E:
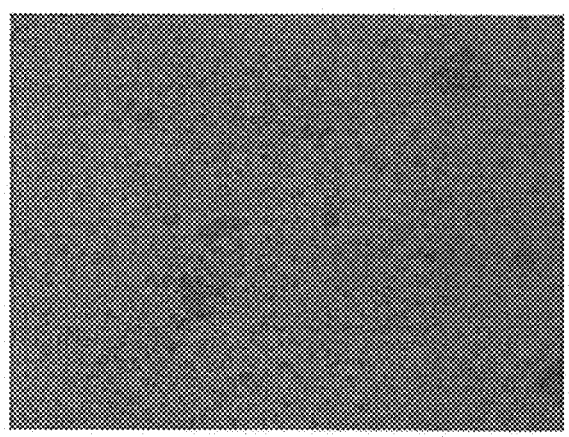
Figure 7F:
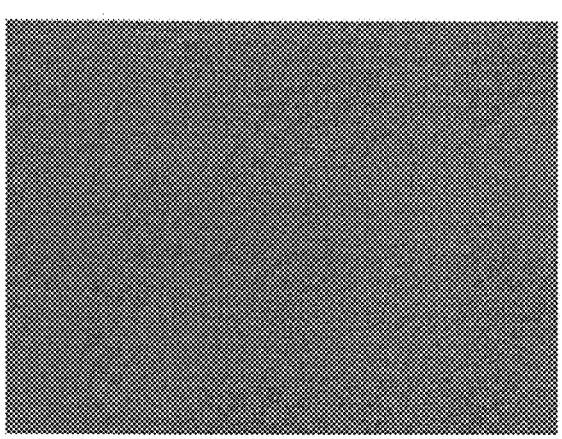
Figure 8:
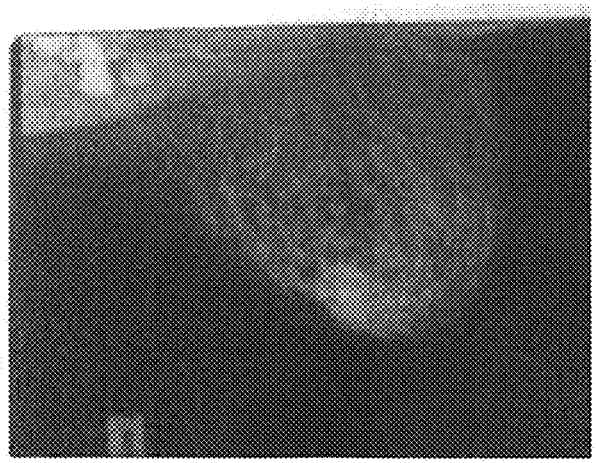
FIG. 8: illustrates tumor in breast by Mammography (WASFYIA).
Figure 9:
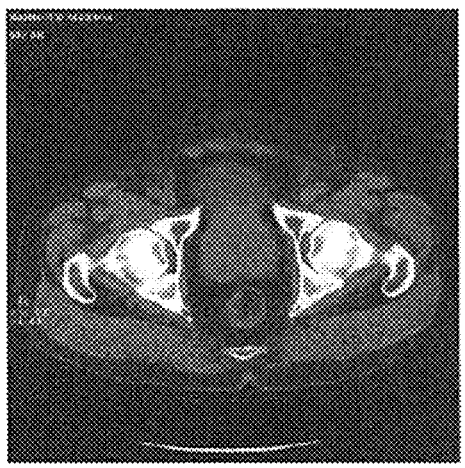
FIG. 9: illustrates the magnitude of the prostate by CT scan (prostate cancer—before treatment (MAHMOUD AL-HOMSI).
Figure 10:
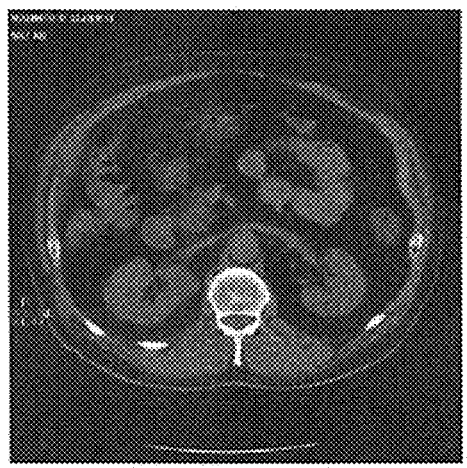
FIG. 10: illustrates metastases from prostate on kidneys by CT scan before treatment (MAHMOUD AL-HOMSI).
Figure 11:
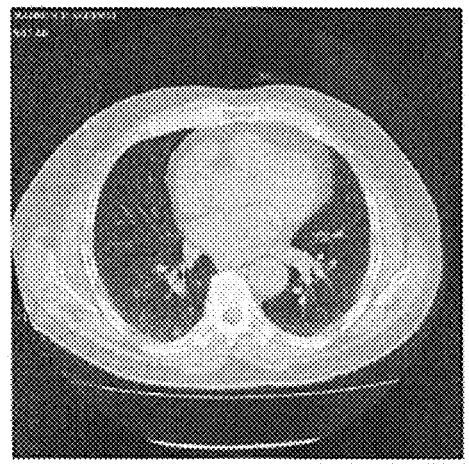
FIG. 11: illustrates metastases from prostate on lungs by CT scan before treatment (MAHMOUD AL-HOMSI).
Figure 12:
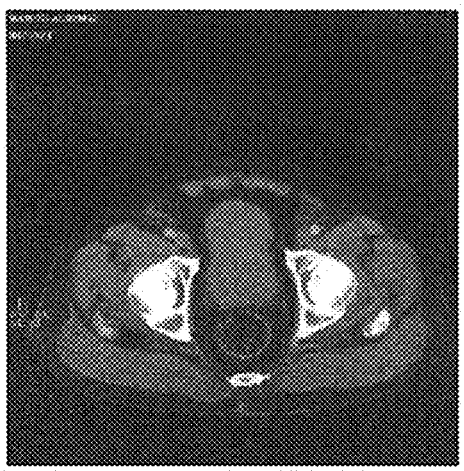
FIG. 12: illustrates CT scan for prostate. The prostate became smaller during treatment with product (MAHMOUD ALHOMSI).
Figure 13:
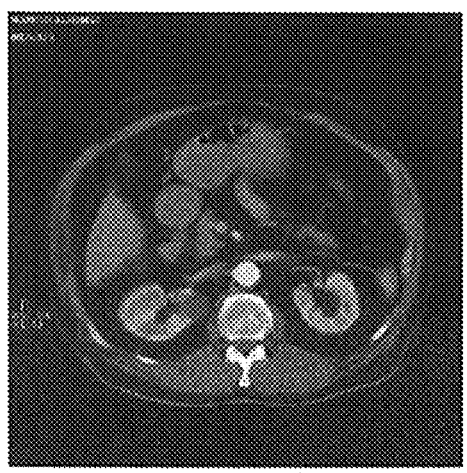
FIG. 13: illustrates CT scan for metastases on the kidneys became smaller during Treatment with product (MAHMOUD ALHOMSI).
Figure 14:
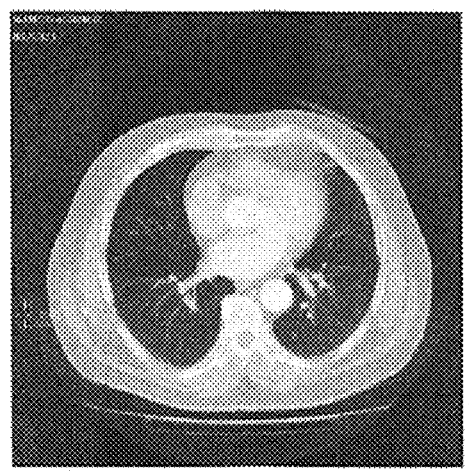
FIG. 14: illustrates CT scan for metastases on lungs became smaller during Treatment with product (MAHMOUD ALHOMSI).
Figure 15:
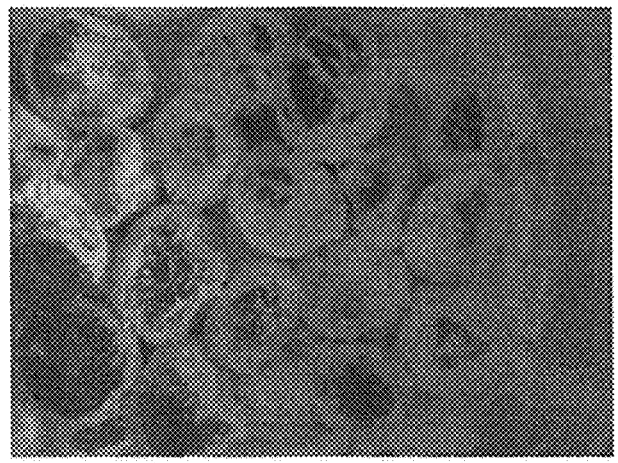
FIG. 15: illustrates growth of on figs.

Put 20 kg of fresh figs in a clean glass and fill this glass with water (15 liter of sterile water). Put a glass in a temperature of 37.5 Celsius, there should be a fan to spread the warm humid air. After 10 to 15 days, take many small pieces of figs and put they on agar after growing *Staphylococcus*, put the agar in 37.5° C. for 24 hours see halo around figs pieces as illustrated in FIGS. 1A and 1B. In one example, take many figs from that glass and put the figs in a new glass, put many fresh or dry figs and full the glass water (each 2 kg of figs need 1.5 liter of sterile water), put it in 37.5° C. for 5 days, take the glass out and put its content in a clean fruits mixer, add a liter of distilled water to it, turn on the mixer for 15 minutes approximately, then filter the mix by a gauze. In another example, put a big amount of the figs in 37.5° C. degrees and in 80 percent degree of humidity for 10-15 days after that *Acetobacter pasteurianus* was grew a lot. These are very suitable circumstances to grow some microorganisms which feed on the materials in the figs. The microorganisms ferment some materials in figs. The result of that some materials which are very important in medicine are produced (antibiotic, anti-viruses, anticancer, and enzymes). the first time these materials are extracted in the world. If the temperature is less than 20° C. or the period of the Incubation is less than 4 days, can't get the required pharmaceutical composition. After manufacturing the pharmaceutical composition it must preserve it in a 6° C. This new pharmaceutical composition is distinguished by fast efficiency.

After that, Test the sensitivity of the product against pathogenic bacteria such as *streptococcus*. incubate it for 24 hours. If it had a halo around it, this means that manufacturing it was correct and without mistakes See FIGS. 1A and 1B.

After manufacturing the pharmaceutical composition it must preserve it in the temperature of 6° Celsius.

Chose 8 groups, each group comprising 3 cups. Put 1 ml natural product in each cup (1 ml natural product contains microorganisms).
Group No. 1: Put in each cup 30 g sucrose+100 ml sterile water+1 ml natural product (containing microorganisms)
Group No. 2: Put in each cup 30 g Glucose+100 ml sterile water+1 ml product
Group No. 3: Put in each cup 30 g Fructose+100 ml sterile water+1 ml product
Group No. 4: Put in each cup 30 g Dextrose+100 ml sterile water+1 ml product
Group No. 5: Put in each cup 50 g pieces of apple+100 ml sterile water+1 ml product
Group No. 6: Put in each cup 50 g pieces of grapes+100 ml sterile water+1 ml product
Group No. 7: Put in each cup 50 g pieces of dates+100 ml sterile water+1 ml product
Group No. 8: Put in each cup 50 g pieces of figs+100 ml sterile water+1 ml product Put all the cups in temperature 37.5° C. for one week. The product (Group No. 8) that made from fermented figs better than products of all the other Groups.

The experiments in which fermentation extracts were used for each: grapes, apples and dates for treatment of sick animals and sick birds (smallpox, for example), results of treatment were some improvements While improving was faster when used the products of the fermentation of figs.

The analysis the extracts of fermenting figs using GC-MS technique, The analysis extracts of fermenting grapes using a technique GC-MS.

The substances which produce from the fermentation of the grapes differ from substances which produce from the fermentation of figs, the microorganisms were watched under a microscope. The microorganisms intensity in the fig product were more than the microorganisms intensity in product of grapes, apples and dates. the fig contains materials which be the favorite food for these microorganisms, so was active, the growing was faster and produce useful substances.

And thus be secretions many microorganisms which grow on fig are very important.

These bacteria that grow on the figs are resistant for the antibiotics.

Product contains: calcium, phosphorus, potassium, chlorine, sodium, copper, iron and manganese.

Put figs+water then boil the mixture and then put the boiled mixture in Colander, take the liquid from under the colander and add for it a nitrate agar, then put new mix (nitrate agar+liquid of figs) inside autoclave. then put the mix in Petri dishes. When Agar become solid grow bacteria of natural product (*Acetobacter pasteurianus*) on Agar and put the Petri dishes in temperature 37.5° C.

After 24 hours the bacteria grow. After 72 hours do a scrape to the white layer surface of Agar, Put it in 100 ml sterile water mix it very well, then put the mix in clean colander.

This liquid drank it patient boy with brain cancer and his health was getting better within 48 hours. As will be readily evident to those skilled in the art, this invention may easily be produced in other definite forms without leaving from its scope or essential characteristics. These examples are, therefore, to be considered as only illustrative and not restrictive, the scope of the invention being indicated by the claims rather than the former description.

FIGS. 20-23 and Tables F1-F4 relate to a study to determine the potency of novel natural extract compounds in inhibiting the proliferation of Normal Human Dermal Fibroblast cell line (NHDF cells). Percent proliferation of cells is calculated at different dilutions of the natural extract compounds and this data is used to calculate the IC50 (X) for the novel natural extract compounds. In this study: Compound I, III and IV which are arrangements of compound according to the present invention are evaluated in a XTT proliferation assay for 72 hours to determine its potency in inhibiting the proliferation of NHDF cells.

Traditionally, the in-vitro determination of toxic effects of unknown compounds has been performed by counting viable cells after staining with a vital dye. The XTT system is a mean of measuring the activity of living cells via mitochondrial dehydrogenases. The XTT method is simple, accurate and yields reproducible results. The key component is the sodium salt of (2,3-bis[2-Methoxy-4-nitro-5-sulfophenyl]-2 H-tetrazolium-5-carboxyanilide inner salt) or XTT.

Solutions of XTT, prepared in medium or balances salt solutions without phenol red, are yellowish in colour. Mitochondrial dehydrogenases of viable cells cleave the tetrazolium ring of XTT yielding orange formazon crystals which are soluble in aqueous solutions. The resulting orange colour is spectrophotometrically measured. The bio-reduction is XTT is inefficient but can be potentiated by the addition of an electron coupling agent such as phenazine methosulphate (PMS) to the reaction. An increase or decrease in cell numbers results in a concomitant change in the amount of formazon formed, indicating the degree of cytotoxicity caused by the test material.

In the foregoing study the following kits and reagents were used:

Cells: NHDF, a Normal Human Dermal Fibroblast cell line (Lonza)
Media: FGM-2 bullet kit media
Cell culture T75 flasks (BD-Falcon-LAB353136)
96 well cell clear tissue culture treated plates (BD-Falcon-LAB353072)
Dimethyl Sulphoxide (DMSO) (Sigma-D2650)
XT (Sigma-X4251)
PMS (Sigma-P9625)

In the foregoing study, three arrangement of compound according to the present invention, which in FIGS. 20-23 and Tables F1-F4 are designated as compounds I, III and IV, were tested.

In the foregoing study, the control or vehicle was sterile deionized water.

In regard to experimental procedure, for seeding in a 96-well plate, the cells were re-suspended to a density of $0.2\times10^5$ cells/ml of complete FGM-2 Bullet kit medium. 80 µL of this cell suspension was added per well to seed ~2000 cells per well. The plate was incubated for 24 hours in an incubator with 5% CO2 at 37° C. before compound addition.

In the foregoing study, the following points relate to compound dilution and treatment:

20 µL of stock (100×) was serially diluted (2×) in 20 µL of sterile deionized water.
20 µL of each dilution was then added in triplicates in the previously seeded 96-well plate.
Cells treated with deionized water served as control.
100 µL of complete Ham's F12 medium served as media blank for the data analysis.
200 µL of PBS was added in all corner wells of the assay plate. Plate was then incubated for 72 hours in an incubator with 5% $CO_2$ at 37° C.

In the foregoing study, the following points relate to termination:

XTT reagent—1 mg/mL solution of XTT was made in serum-free Ham's F12 medium. Freshly prepared PMS was added to the XTT solution such that the final concentration of PMS was 25 µM.
100 µL of the XTT reagent was added to each well and the plate was incubated in a CO2 incubator at 37° C. until color development.
The assay plates were read at 450 nm using Victor X5 Multilabel Plate Reader (Perkin-Elmer). The data was analyzed using GraphPad Prism Software.

In regard to data generation in the foregoing study:

Raw data of OD values was obtained in the form of excel sheet from Victor X5 Multi-label Plate Reader.
Average of media blank and average of control was calculated.
Average media blank was subtracted from each experimental well and control. Blank subtracted values were used to calculate % inhibition.
Percent (%) inhibition is calculated by normalizing control values to 100% using the formula, % Inhibition=100−[(OD sample/OD control)*100]
% Inhibition was plotted against the respective concentrations of compounds in GraphPad Prism to calculate $IC_{50}$ value FIGS. 20-23 in conjunction with Tables F1-F4 show the results of the afore-described tests, from which it can be concluded that all compounds tested were minimally toxic to NHDF, a normal human dermal fibroblast cell.

FIGS. 24-27 and Tables G1-G4 relate to a study to determine the potency of novel natural extract compounds in inhibiting the proliferation of a fibrosarcoma cell line (HT-1080 cells). Percent proliferation of cells is calculated at different dilutions of the natural extract compounds and this data is used to calculate the IC50 (X) for the novel natural extract compounds. In this study: Compound I, III and IV which are arrangements of compound according to the present invention are evaluated in a XTT proliferation assay for 72 hours to determine its potency in inhibiting the proliferation of HT-1080 cells.

In the foregoing study the following kits and reagents were used:

Cells: HT-1080, a fibrosarcoma cell line (ATCC® CCL-121™)
Media: MEM media (Sigma-M0268)
FBS-Fetal Bovine serum (Sigma-F7524)
Penicillin streptomycin (Gibco-15140-122)
Cell culture T75 flasks (BD-Falcon-LAB353136)
96 well cell clear tissue culture treated plates (BD-Falcon-LAB353072)
Dimethyl Sulphoxide (DMSO) (Sigma-D2650)
XTT (Sigma-X4251)
PMS (Sigma-P9625)

In the foregoing study, three arrangement of compound according to the present invention, which in FIGS. 24-27 and Tables G1-G4 are designated as compounds I, III and IV, were tested.

In the foregoing study, the control or vehicle was sterile deionized water.

In regard to the experimental procedure for the foregoing study, for seeding in a 96-well plate, the cells were re-suspended to a density of $0.1\times10^5$ cells/ml of complete MEM medium. 80 µL of this cell suspension was added per well to seed ~1000 cells per well. The plate was incubated for 24 hours in an incubator with 5% CO2 at 37° C. before compound addition.

In the foregoing study, the following points relate to compound dilution and treatment:

20 µL of stock (100×) was serially diluted (2×) in 20 µL of sterile deionized water.
20 µL of each dilution was then added in triplicates in the previously seeded 96-well plate.
Cells treated with deionized water were served as control.
100 µL of complete Ham's F12 medium served as media blank for the data analysis.
200 µL of PBS was added in all corner wells of the assay plate. Plate was then incubated for 72 hours in an incubator with 5% $CO_2$ at 37° C.

In the foregoing study, the following points relate to termination:

XTT reagent—1 mg/mL solution of XTT was made in serum-free Ham's F12 medium. Freshly prepared PMS was added to the XTT solution such that the final concentration of PMS was 25 µM.

100 µL of the XTT reagent was added to each well and the plate was incubated in a $CO_2$ incubator at 37° C. until color development.

The assay plates were read at 450 nm using Victor X5 Multilabel Plate Reader (Perkin-Elmer). The data was analyzed using GraphPad Prism Software.

In regard to data generation in the foregoing study:

Raw data of OD values was obtained in the form of excel sheet from Victor X5 Multilabel Plate Reader.

Average of media blank and average of control was calculated.

Average media blank was subtracted from each experimental well and control. Blank subtracted values were used to calculate % inhibition.

Percent (%) inhibition is calculated by normalizing control values to 100% using the formula, % Inhibition=100−[(OD sample/OD control)*100]

% Inhibition was plotted against the respective concentrations of compounds in GraphPad Prism to calculate $IC_{50}$ value FIGS. 24-27 in conjunction with Tables G1-G4 show the results of the afore-described tests, from which it can be concluded that compounds I, III and IV show high potency on inhibition of proliferation of HT-1080, a fibrosarcoma cell.

Experiments have shown that this product is completely safe, its taste is acceptable, and it does not have any side effects.

It will be a great hope to meet the market's need to this product especially after producing it chemically in drugs companies The scope of the claims should not be limited by the preferred embodiments set forth in the examples but should be given the broadest interpretation consistent with the specification as a whole.

Tables

TABLE F1

Inhibition of Doxorubicin on NHDF cells.

| Doxorubicin (µM) | % Inhibition |
|---|---|
| 3 | 57.1 |
| 1 | 86.4 |
| 0.33 | 68.6 |
| 0.11 | 37.5 |
| 0.04 | 33.9 |
| 0.01 | 26.9 |
| 0.004 | 25.9 |
| 0.001 | 17.9 |
| 0.000 | 24.6 |

TABLE F2

Inhibition of Compound I on NHDF cells.

| Compound I (x) | % Inhibition |
|---|---|
| 100 | 52.4 |
| 50.0 | 13.2 |
| 25.0 | 16.1 |
| 12.5 | 16.4 |
| 6.3 | 25.9 |
| 3.1 | 32.0 |
| 1.6 | 29.2 |
| 0.8 | 22.2 |
| 0.4 | 35.6 |

TABLE F3

Inhibition of Compound III on NHDF cells.

| Compound III (x) | % Inhibition |
|---|---|
| 100 | 73.1 |
| 50.0 | 88.3 |
| 25.0 | 27.6 |
| 2.5 | 8.5 |
| 6.3 | −2.5 |
| 3.1 | −5.7 |
| 1.6 | 6.2 |
| 0.8 | 0.0 |
| 0.4 | 9.9 |

TABLE F4

Inhibition of Compound IV on NHDF cells.

| Compound IV (x) | % Inhibition |
|---|---|
| 100 | 88.7 |
| 50.0 | 44.1 |
| 25.0 | −3.9 |
| 12.5 | 1.2 |
| 6.3 | 9.9 |
| 3.1 | 15.9 |
| 1.6 | 17.8 |
| 0.8 | 14.6 |
| 0.4 | 18.6 |

TABLE G1

Inhibition of Doxorubicin on HT-1080 cells.

| Doxorubicin (µM) | % Inhibition |
|---|---|
| 1 | 98.25 |
| 0.3333 | 90.96 |
| 0.1111 | 77.69 |
| 0.0370 | 76.4 |
| 0.0123 | 63.61 |
| 0.0041 | 28.95 |
| 0.0014 | 22.13 |
| 0.0005 | 14.86 |
| 0.0002 | 16.06 |

TABLE G2

Inhibition of Compound I on HT-1080 cells.

| Compound I (X) | % Inhibition |
|---|---|
| 100 | 102.38 |
| 50.0 | 91.84 |
| 25.0 | 93.52 |
| 12.5 | 98.19 |
| 6.3 | 100.60 |
| 3.1 | 104.10 |
| 1.6 | 104.88 |
| 0.8 | 97.28 |
| 0.4 | 74.43 |

TABLE G3

Inhibition of Compound III on HT-1080 cells.

| Compound III (X) | % Inhibition |
|---|---|
| 100 | 91.20 |
| 50.0 | 96.41 |
| 25.0 | 91.87 |
| 12.5 | 76.09 |
| 6.3 | 71.68 |
| 3.1 | 59.40 |
| 1.6 | 51.04 |
| 0.8 | 42.48 |
| 0.4 | 37.76 |

TABLE G4

Inhibition of Compound IV on HT-1080 cells.

| Compound IV (X) | % Inhibition |
|---|---|
| 100 | 97.58 |
| 50.0 | 77.19 |
| 25.0 | 61.95 |
| 12.5 | 54.88 |
| 6.3 | 50.96 |
| 3.1 | 38.83 |
| 1.6 | 44.84 |
| 0.8 | 39.76 |
| 0.4 | 31.16 |

The invention claimed is:

1. A pharmaceutical composition comprising an aqueous extract prepared by growing *Acetobacter pasteurianus* on figs, recovering bacterial growth therefrom, suspending the bacterial growth in water to form a suspension, and filtering the suspension.

2. The pharmaceutical composition according to claim 1 wherein the *Acetobacter pasteurianus* is grown on a solid medium made of Nitrate Agar and fig liquid.

3. The pharmaceutical composition according to claim 1 wherein the *Acetobacter pasteurianus* grows on the figs and the *Acetobacter pasteurianus* feeds on substances in the figs.

4. The pharmaceutical composition according to claim 1 produced by fermentation of the figs by the *Acetobacter pasteurianus*.

5. A pharmaceutical composition according to claim 1 for use to improve immune response.

6. A pharmaceutical composition according to claim 1 for use in inflammatory treatment.

7. The pharmaceutical composition according to claim 2 wherein the aqueous extract is prepared from a layer of bacterial growth scraped from a surface of the solid medium.

\* \* \* \* \*